United States Patent
Nikolski et al.

(10) Patent No.: US 11,134,984 B2
(45) Date of Patent: Oct. 5, 2021

(54) PRESSURE-SENSING IMPLANT TOOLS

(71) Applicant: Medtronic, Inc., Minneapolis, MN (US)

(72) Inventors: Vladimir P. Nikolski, Blaine, MN (US); Linnea R. Lentz, Stacy, MN (US); Amy E. Thompson-Nauman, Ham Lake, MN (US); Teresa A. Whitman, Dayton, MN (US); Mark T. Marshall, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 574 days.

(21) Appl. No.: 16/050,626

(22) Filed: Jul. 31, 2018

(65) Prior Publication Data

US 2020/0038060 A1 Feb. 6, 2020

(51) Int. Cl.
*A61B 5/00* (2006.01)
*A61B 17/34* (2006.01)
(Continued)

(52) U.S. Cl.
CPC .... *A61B 17/3468* (2013.01); *A61B 17/00234* (2013.01); *A61B 17/3415* (2013.01);
(Continued)

(58) Field of Classification Search
CPC .......... A61B 17/3468; A61B 17/00234; A61B 17/3415; A61B 2017/320056; A61B 2090/064; A61B 17/320016; A61N 1/0504; A61N 1/3968; A61M 25/008; A61M 25/0194
(Continued)

(56) References Cited

U.S. PATENT DOCUMENTS 6,770,070 B1   8/2004  Balbierz
6,920,878 B2 * 7/2005  Sinderby ............ A61M 16/026
                                                128/204.23
(Continued)

OTHER PUBLICATIONS (PCT/US2019/044265) PCT Notification of Transmittal of the International Search Report and the Written Opinion of the International Searching Authority, dated Oct. 9, 2019, 13 pages.
(Continued)

*Primary Examiner* — May A Abouelela
(74) *Attorney, Agent, or Firm* — Shumaker & Sieffert, P.A.

(57) ABSTRACT

In some examples, a system includes a medical device comprising an elongate body configured to advance through layers of tissue of a patient, a lumen extending through the elongate body, a fluid line configured to supply fluid to the lumen, and a pressure sensor positioned within the lumen or the fluid line. The system may further include processing circuitry configured to receive, from the pressure sensor, a signal corresponding to the pressure of the fluid at each of a plurality of time points, determine, for each time point: a corresponding amplitude value of the signal, a difference between two amplitude values of the signal, an amplitude oscillation status of the signal, a position of the elongate body based on the difference and the amplitude oscillation status; and provide an indication of the position of the elongate body relative to the layers of tissue.

41 Claims, 14 Drawing Sheets

(51) Int. Cl.
 *A61B 17/00*    (2006.01)
 *A61M 25/00*    (2006.01)
 *A61N 1/05*    (2006.01)
 *A61B 17/32*    (2006.01)
 *A61M 25/01*    (2006.01)
 *A61N 1/39*    (2006.01)

(52) U.S. Cl.
 CPC ......... *A61M 25/008* (2013.01); *A61N 1/0504* (2013.01); *A61B 17/3494* (2013.01); *A61B 2017/00331* (2013.01); *A61B 2017/320056* (2013.01); *A61M 25/0194* (2013.01); *A61N 1/3968* (2013.01)

(58) Field of Classification Search
 USPC .................. 600/561, 587, 595; 606/124, 129
 See application file for complete search history.

(56) References Cited

U.S. PATENT DOCUMENTS

| | | | |
|---|---|---|---|
| 7,890,191 B2 | 2/2011 | Rutten et al. | |
| 8,328,738 B2 | 12/2012 | Frankhouser et al. | |
| 8,777,871 B2 | 7/2014 | Frankhouser et al. | |
| 9,218,752 B2 * | 12/2015 | Gillies | G09B 23/28 |
| 9,468,396 B2 * | 10/2016 | Mahapatra | A61B 5/03 |
| 9,642,534 B2 * | 5/2017 | Mahapatra | A61B 5/316 |
| 9,642,555 B2 | 5/2017 | Bonner et al. | |
| 2003/0100845 A1 * | 5/2003 | Eide | A61B 5/021 |
| | | | 600/561 |
| 2007/0032796 A1 * | 2/2007 | Chin-Chen | A61B 17/0057 |
| | | | 606/139 |
| 2009/0275956 A1 * | 11/2009 | Burnes | A61N 1/05 |
| | | | 606/129 |
| 2010/0331854 A1 * | 12/2010 | Greenberg | A61B 17/3421 |
| | | | 606/129 |
| 2012/0172750 A1 * | 7/2012 | Sawyer | A61B 5/03 |
| | | | 600/561 |
| 2012/0184862 A1 * | 7/2012 | Foo | A61B 5/113 |
| | | | 600/508 |
| 2012/0330184 A1 | 12/2012 | Mahapatra et al. | |
| 2014/0235960 A1 * | 8/2014 | Addington | A61B 5/037 |
| | | | 600/301 |
| 2014/0243703 A1 * | 8/2014 | Schmidt | A61B 5/031 |
| | | | 600/561 |
| 2014/0276198 A1 * | 9/2014 | Dunung | A61B 5/03 |
| | | | 600/561 |
| 2014/0276925 A1 * | 9/2014 | Alves | A61B 17/3468 |
| | | | 606/129 |
| 2015/0282753 A1 * | 10/2015 | Ahmadi | A61B 5/391 |
| | | | 600/301 |
| 2015/0343176 A1 | 12/2015 | Asleson et al. | |
| 2016/0000325 A1 * | 1/2016 | Cao | A61B 5/6839 |
| | | | 600/398 |
| 2016/0008593 A1 * | 1/2016 | Cairns | A61N 1/0551 |
| | | | 606/129 |
| 2016/0022222 A1 * | 1/2016 | Folk | A61B 6/032 |
| | | | 623/1.15 |
| 2016/0067478 A1 | 3/2016 | McGeehan et al. | |
| 2016/0128575 A1 * | 5/2016 | Chuang | F03G 1/10 |
| | | | 600/587 |
| 2016/0175584 A1 | 6/2016 | Drake et al. | |
| 2017/0007287 A1 | 1/2017 | Malewicz et al. | |
| 2017/0056115 A1 | 3/2017 | Corndorf et al. | |
| 2017/0312509 A1 * | 11/2017 | Bauer | A61B 5/021 |
| 2019/0201037 A1 * | 7/2019 | Houser | A61B 34/37 |
| 2019/0201046 A1 * | 7/2019 | Shelton, IV | A61B 90/361 |
| 2019/0247050 A1 * | 8/2019 | Goldsmith | A61B 17/00491 |

OTHER PUBLICATIONS

Baudoin, et al., "The superior epigastric artery does not pass through Larrey's space (trigonum sternocastale)," Surg. Radiol. Antat. 25.3-4, Aug. 2003, pp. 259-262.

\* cited by examiner

PRESSURE-SENSING IMPLANT TOOLS

TECHNICAL FIELD

This disclosure relates generally to medical device systems and, more particularly, to implant tool systems configured for traversing multiple layers of tissues during a medical procedure, such as a medical procedure for implanting medical leads or other implantable components.

BACKGROUND

Some medical procedures may include crossing multiple tissue layers to gain access to a location within the body of a patient. Such medical procedures may include implanting one or more medical devices or components thereof at the location, e.g., medical electrical leads, or placing a chest tube, trocar, or other device, e.g., for minimally invasive surgery. One manner of accessing an intrathoracic location is substernally, e.g., via subxiphoid access, and includes traversing one or more layers of tissue, e.g., diaphragmatic attachments that attach the diaphragm to the sternum. Examples of such procedures involving access to an intrathoracic location include epicardial ablation, procedures involving pericardial access, pericardiocentesis, procedures involving pleural cavity access, or the implantation of the distal portions of one or more leads substernally, and may include using an implant tool to access the intrathoracic cavity of the patient. In the example of lead implantation, the one or more leads may be part of an implantable cardiac defibrillator (ICD) system that may be used to deliver high-energy electrical pulses to the patient's heart to terminate life threatening cardiac arrhythmias, such as ventricular fibrillation. Such ICDs may include, or may be part of a system that includes, a subcutaneously-implantable housing that may enclose a pulse generator or other electronics of an ICD. The housing of some ICDs may be connected to the one or more leads, which may be configured to deliver defibrillation and/or pacing pulses.

SUMMARY

In general, this disclosure is directed to examples of implant tools that include one or more pressure sensors for medical procedures that traverse multiple layers of tissue and techniques utilizing such tools. Such techniques may include monitoring a pressure within or at a leading edge of the implant tool during a procedure to advance the implant tool through one or more layers of tissue. The techniques may include determining when the implant tool has crossed through a layer of the one or more layers of tissue based on the monitored pressure, which may provide feedback to the clinician regarding the progress of the procedure.

As an example, the tools and techniques may be used to cross one or more layers of tissue between the skin and an intrathoracic cavity of a patient, and determine when the implant tool has crossed through a layer of the one or more layers of tissue based on a drop in pressure and/or the appearance of respiratory pressure oscillations as the implant tool is advanced. Such a determination may enable a clinician using the tool to determine when additional layers of tissue between the skin and the anterior mediastinum remain uncrossed, and to determine when the implant tool has advanced past each of the one or more layers of tissue into an anterior mediastinum of the patient. Once the implant tool has advanced into the anterior mediastinum, a distal portion of a medical lead, e.g., of an ICD system, may be implanted in the anterior mediastinum. In some examples, the intrathoracic cavity of the patient may include one or more of an anterior mediastinum, a posterior mediastinum, a middle mediastinum (which includes the pericardium and pericardial cavity), a pleural cavity, or a superior mediastinum of the patient. Although the tools and techniques are described herein primarily in the context of crossing layers of tissue between the skin and the anterior mediastinum and implanting a medical lead within the anterior mediastinum, the tools and techniques are applicable to implanting a medical lead or other device within any portion of the intrathoracic cavity of the patient.

Because transvenous leads may not be preferred for all patients, ICD systems that include one or more extravascular leads may be preferred for some patients. During some example procedures to implant an extravascular lead, a clinician may create a path through patient tissue from an access site to a lead placement site by tunneling an implant tool through the tissue via blunt dissection or needle techniques. In some examples, the lead placement site may be in an anterior mediastinum of the patient, posterior to the sternum and anterior to the pericardium. Due to the relative locations of the sternum, the anterior mediastinum, and the diaphragm, the path through the tissue may extend between the diaphragm and the xiphoid process, through one or more layers of tissue that connect the diaphragm to the sternum (which may be referred to as or include diaphragmatic attachments), and into the anterior mediastinum. After the clinician has created the path from the access site to the lead placement site, the clinician may introduce the lead through the path, such as via an introducer sheath, and complete any remaining steps in the implant procedure.

In some such example procedures, it may be advantageous for the clinician to determine when the implant tool crosses each of the layers of the of the diaphragmatic attachments, as well as when the implant tool has crossed all of the layers of the diaphragmatic attachments. For example, by determining when the implant tool crosses one of the layers of the diaphragmatic attachments, the clinician may determine how many layers of the diaphragmatic attachments remain uncrossed, which may indicate that the clinician should further advance the implant tool. By determining when the implant tool has crossed all of the layers of the diaphragmatic attachments, the clinician may be able to determine when to stop advancing the implant tool, change the direction of advancement of the implant tool, or withdraw the implant tool and replace it with a different device. In addition, the clinician thus may avoid advancing the implant tool into unintended contact with the pericardium or other non-target tissues of the patient, thereby lowering a likelihood of unintended punctures, abrasion, or other adverse effects of such unintended contact. Further, the clinician may identify contact with the sternum based on a higher degree of contact force and/or more persistent force exerted by the sternum on the implant tool than would be exerted by the one or more layers of the diaphragmatic attachments or other tissues, such as the pericardium. Directing the implant tool toward the underside of the sternum during implant may confer safety because the tool may thereby be directed away from the pericardium, heart, or other non-target tissues. A change in pressure exerted by patient tissue upon the implant tool, subsequent to crossing each of the layers of the diaphragmatic attachments, may indicate desired contact with the sternum.

However, a clinician may have difficulty determining, unaided, when the implant tool has crossed one or more of the layers of the diaphragmatic attachments. For example, it may be difficult for the clinician to distinguish a tactile sensation of advancing the implant tool through the layers of the diaphragmatic attachments from a tactile sensation of advancing the implant tool through other types of tissue. Thus, systems for enabling a clinician to determine a position of an implant tool relative to one or more layers of the diaphragmatic attachments may include a pressure-sensing medical device, such as the pressure-sensing medical devices described herein.

For example, systems described herein may be configured to provide information indicative of a position of one or more portions of an implant tool within a patient, based on changes in a pressure of a fluid (e.g., a liquid or a gas) within a lumen of an elongate body of the implant tool and/or a lumen of a fluid line connected to a lumen of the elongate body, as sensed by at least one pressure sensor positioned within the lumen of the elongate body or the lumen of the fluid line. In some examples, the lumen of the elongate body may extend to a distal end of the elongate body, such that fluid flowing through the lumen of the elongate body encounters resistance from a layer of tissue of the patient (e.g., a diaphragmatic attachment) when the distal end of the elongate body is in contact with the layer of tissue. As a clinician advances the implant tool, the pressure of the fluid may drop as the distal end of the elongate body crosses the layer of tissue, relative to when the distal end of the elongate body is in contact with (e.g., within) the layer of tissue. When the layer of tissue is a deepest one of a plurality of layers of tissue to be crossed, oscillations in an amplitude of the pressure of the fluid may be observed as the distal end of the elongate body crosses the layer of tissue. Such oscillations may be associated with respiration of the patient, such that the appearance of the oscillations is indicative of the distal end of the implant tool having crossed each of the plurality of layers of tissue and entered an anterior mediastinum of the patient.

In some examples, the systems described herein may include processing circuitry configured to receive a signal corresponding to a pressure of the fluid from the pressure sensor, and provide, via a user interface, an indication to the clinician that the elongate body of the implant tool has crossed one or more of the diaphragmatic attachments of the patient. Such indications may be audible, visible, or tactile in nature. In some examples, such indications may indicate a position of the distal end of the elongate body relative to other layers of the plurality of layers of tissue. For example, the indication may include one audible tone when the distal end of the elongate body crosses a first layer of tissue and may include two audible tones when the distal end of the elongate body crosses a second layer of tissue. In any such examples, the systems and techniques described herein may increase the clinician's awareness of the position of a distal end of an elongate body of an implant tool during a procedure to advance the elongate body through patient tissue, which may lead to safer, more efficient medical procedures and improved clinical outcomes for the patient.

In one example, a system for determining a position of a medical device relative to a plurality of layers of tissue of a patient comprises: the medical device comprising: an elongate body defining a proximal end and a distal end configured to advance through the plurality of layers of tissue; and at least one pressure sensor, wherein the at least one pressure sensor is configured to sense a pressure during a medical procedure to advance the elongate body through the plurality of layers of tissue of the patient; and processing circuitry configured to: receive, from the at least one pressure sensor, a signal corresponding to the pressure at each of a plurality of time points during the medical procedure; determine, for each of the plurality of time points, a corresponding amplitude value of the signal; determine a difference between two amplitude values of the signal; determine an amplitude oscillation status of the signal; determine, based on the difference between the two amplitude values and the amplitude oscillation status, a position of the distal end of the elongate body relative to the plurality of layers of tissue; and provide, via a user interface, an indication of the position of the distal end of the elongate body relative to the plurality of layers of tissue.

In another example, a method for determining a position of a medical device relative to a plurality of layers of tissue of a patient, the medical device comprising: an elongate body defining a proximal end and a distal end configured to advance through the plurality of layers of tissue; at least one pressure sensor, wherein the at least one pressure sensor is configured to sense a pressure while advancing the elongate body through the plurality of layers of tissue of a patient; and the method comprising, by processing circuitry of a medical device system comprising the medical device: receiving, from the at least one pressure sensor, a signal corresponding to the pressure at each of a plurality of time points during the medical procedure; determining, for each of the plurality of time points, a corresponding amplitude value of the signal; determining a difference between two amplitude values of the signal; determining an amplitude oscillation status of the signal; determining, based on the difference between the two amplitude values and the amplitude oscillation status, a position of the distal end of the elongate body relative to the plurality of layers of tissue; and providing, via a user interface, an indication of the position of the distal end of the elongate body relative to the plurality of layers of tissue.

In another example, a medical device comprises an elongate body defining a proximal end and a distal end configured to advance through a plurality of tissue layers, and a first lumen extending at least partially through the elongate body to the distal end; and at least one pressure sensor, wherein the at least one pressure sensor is configured to sense a pressure during a medical procedure to advance the elongate body through a plurality of layers of tissue of a patient and transmit to processing circuitry, at each of a plurality of time points during the medical procedure, a signal corresponding to the pressure, wherein a difference between two values of the signal and an amplitude oscillation status of the signal is associated with a position of the distal end of the elongate body relative to the plurality of layers of tissue.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
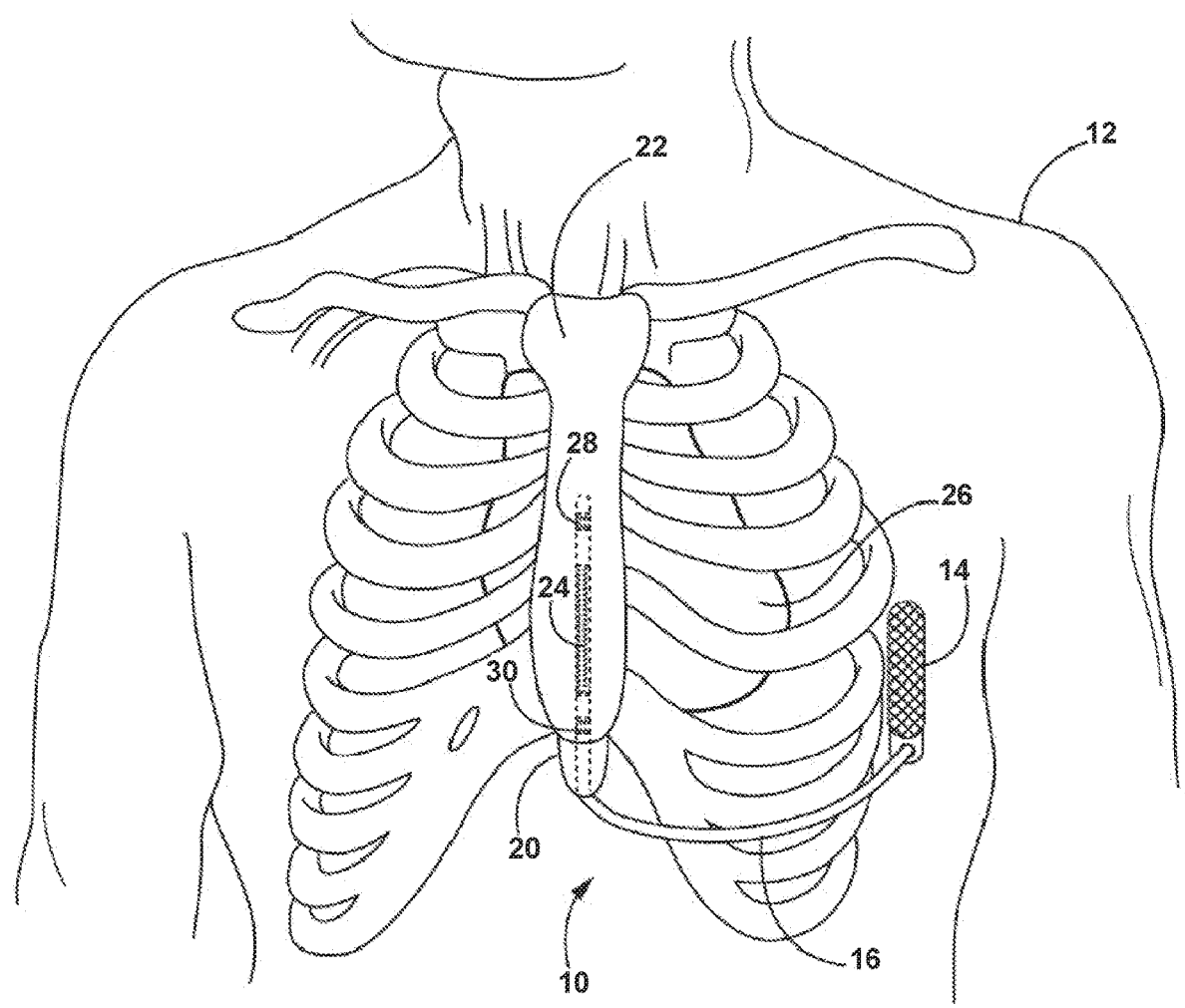
FIG. 1A is a conceptual drawing illustrating a front view of a patient implanted with an example implantable cardiac system having a substernal lead.

In general, this disclosure describes example systems for determining a position of a medical device relative to a plurality of layers of tissue of a patient. Such a medical device may include an elongate body configured to be advanced through the plurality of layers of tissue and into a cavity or other location within the patient, e.g., an intrathoracic cavity, or a portion of an intrathoracic cavity of the patient and at least one pressure sensor configured to sense a pressure during a medical procedure to advance the elongate body through the plurality of layers of tissue. In some examples, a system may include processing circuitry configured to receive, from the pressure sensor, a signal corresponding to each of a plurality of time points during the medical procedure, determine a position of a distal end of the elongate body based on the signal, and provide an indication of the position of the distal end of the elongate body relative to the plurality of layers of tissue. For example, the system may provide an indication that the distal end of the elongate body is within one or more portions of the intrathoracic cavity, such as within one or more of the anterior mediastinum, the posterior mediastinum, the middle mediastinum (which includes the pericardium and pericardial cavity), a pleural cavity, or the superior mediastinum of the patient.

In some examples, the elongate body may define a lumen, and the medical device may further include a fluid line connected to the elongate body and in communication with the lumen defined by the elongate body. In such examples, the pressure sensor may be positioned within one of the lumen defined by the elongate body or a lumen of a fluid line connected to the elongate body. The pressure sensor in such examples may be configured to sense pressure indirectly exerted on it by one or more types of patient tissue (e.g., a layer of the plurality of layers of tissue, a pericardium, a sternum, or any other types of tissue) within the environment in which a lead implantation procedure may be conducted. For example, when a distal end of the elongate body comes into contact with patient tissue, the patient tissue may exert pressure on the fluid supplied to the lumen by the fluid line. In turn, the pressure sensor in such examples may directly sense pressure exerted on it by the fluid supplied to the lumen by the fluid line.

In other examples, the elongate body may not necessarily define a lumen and the medical device may not necessarily include a fluid line connected to the elongate body. In such examples, the pressure sensor may be positioned at or near the distal end of the elongate body, such as on an outer surface of the elongate body. The pressure sensor in such examples may be configured to sense pressure exerted directly upon it by the one or more types of patient tissue within the environment in which the lead implantation procedure may be conducted. Although the tools and techniques are described herein primarily in the context of examples in which an elongate body defines a lumen and a medical device comprises a fluid line connected to the elongate body and in communication with the lumen defined by the elongate body, the tools and techniques are equally applicable to examples in which the elongate body may not necessarily define a lumen and the medical device may not necessarily include a fluid line connected to the elongate body, such as the examples in which the pressure sensor may be positioned at or near a distal end of the elongate body.

In some examples, the processing circuitry may determine the position of the elongate body relative to the plurality of layers of tissue and, in some examples, the anterior mediastinum of the patient based on one or more aspects of the signal corresponding to the pressure of the fluid at one or more of the plurality of time points during the medical procedure. For example, the processing circuitry may determine, for each of the plurality of time points, a corresponding amplitude value of the signal received from the pressure sensor and determine a difference between two of the amplitude values. In some examples, such time points could be set with certain fixed delays or correspond to phases of a breathing cycle or phases of a cardiac cycle. In some examples, the two amplitude values may correspond to two consecutive ones of the plurality of time points. In other examples, the two amplitude values may correspond to non-consecutive ones of the plurality of time points, such as time points separated by one or more others of the plurality of time points. The processing circuitry may also determine an amplitude oscillation status of the signal. The processing circuitry may determine a position of the distal end of the elongate body relative to the plurality of layers of tissue based on the difference between the two amplitude values and the amplitude oscillation status of the signal. In some examples, the processing circuitry provides, via a user interface, an indication of the position of the distal end of the elongate body relative to the plurality of layers of tissue.

The amplitude oscillation status may comprise either an absence or a presence of oscillations in an amplitude of the signal corresponding to the pressure of the fluid. The oscillations may be associated with patient respiratory cycles. For example, pressure exerted by the fluid on the pressure sensor may increase during inspiration and decrease during expiration. Such oscillations associated with respiratory cycles of the patient may be detectable by the pressure sensor, or may exceed an amplitude threshold for oscillation sensing, only when the distal end of the elongate body is positioned deep to each layer of the plurality of layers of tissue and, for example, within the anterior mediastinum. In examples in which the amplitude oscillation status comprises an absence of oscillations in the amplitude values of the signal, an absence of the oscillations may be associated with the distal end of the elongate body being positioned superficial to at least one layer of the plurality of layers of tissue.

In some examples, an oscillation status that comprises an absence of oscillations may correspond to an absence of oscillations that satisfy a threshold amplitude and may include oscillations having an amplitude that does not satisfy the threshold amplitude value, such as sub-threshold oscillations that may be detected by the pressure sensor before the distal end of the elongate body is positioned deep to each layer of tissue of the plurality of layers of tissue. In such examples, the oscillations in pressure that may be associated with respiratory cycles of the patient and may be detectable by the pressure sensor only when the distal end of the elongate body is positioned deep to each layer of the plurality of layers of tissue comprise oscillations having an amplitude that does satisfy the threshold amplitude value. In examples in which the amplitude oscillation status comprises a presence of at least one such oscillation associated with respiratory cycles of the patient in the amplitude values of the signal, such a presence of the at least one oscillation may be associated with the distal end of the elongate body being positioned deep to each layer of the plurality of layers of tissue. Thus, an indication of the position of the distal end of the elongate body relative to the plurality of layers of tissue may include an indication of whether the distal end of the elongate body has crossed each of the plurality of layers of tissue.

In some example systems described herein, a difference between two amplitude values of a pressure signal corresponds to a decrease in the pressure of the fluid that is associated with movement of the distal end of the elongate body from a position within or superficial to a layer of the plurality of layers of tissue to a position deep to the layer of the plurality of layers of tissue. For example, the plurality of layers of tissue may be three layers of tissue, and the decrease in pressure may be associated with movement of the distal end of the elongate body from a position superficial to each of the layers of tissue to a position deep to one of the layers of tissue. In other such examples, the difference between the two amplitude values of the signal may correspond to a decrease in the pressure of the fluid that is associated with movement of the distal end of the elongate body from a position deep to only one of the layers of tissue to a position deep to two or three layers of tissue. Thus, an indication of the position of the distal end of the elongate body relative to the plurality of layers of tissue may include an indication that the distal end of the elongate body is one of superficial to each of the layers of tissue, deep to only one layer of tissue, or deep to each of the layers of tissue.

Because the processing circuitry may provide, via a user interface, an indication of the position of the distal end of the elongate body relative to the plurality of layers of tissue at each of a plurality of time points, the systems described herein may provide a clinician with real-time or near real-time indications of the position of the distal end of the elongate body during a procedure to advance the elongate body through the plurality of layers of tissue of the patient. Such indications of the position of the distal end of the elongate body may enable a clinician to determine when to stop advancing the elongate body, advance the elongate body in a different direction, and/or withdraw the elongate body from the patient and advance a different device through the path created by the elongate body. In addition, such indications of the position of the distal end of the elongate body may help the clinician to avoid unintended contact between the elongate body and the pericardium or other non-target tissues of the patient, thereby lowering a likelihood of unintended punctures, abrasion, or other adverse effects of such unintended contact.

Some other systems and techniques may employ fluoroscopic imaging to determine a position of one or more portions of an elongate body during a medical procedure to advance the elongate body through tissue layers of a patient. Although such systems and techniques may provide direct visualization of the layers of tissue in the path of the elongate body, the fluoroscopy tools needed may be expensive, complex, and/or may not provide information about remaining uncrossed tissue layers that could block the advance of the elongate body. Moreover, the use of fluoroscopy equipment exposes the patient to ionizing radiation. Still other systems and techniques include visible markings on a proximal end of an elongate body, which may enable the clinician to determine how far the elongate body has been advanced. However, such systems and techniques may not account for between-patient anatomical variations, such as the location and/or thickness of the layers of tissue, and thus may not provide an accurate indication of a position of the elongate body relative to the layers of tissue of a specific patient.

In some example systems and techniques described herein, a position of a distal end of an elongate body may be accurately determined during a medical procedure to advance the elongate body through a plurality of layers of tissue of a patient, by sensing a pressure of a fluid within a lumen of the elongate body and/or a lumen of a fluid line connected to the elongate body. Drops in pressure and oscillations in an amplitude of a pressure signal may indicate a position of the distal end of the elongate body relative to the layers of tissue of the patient. Thus, in some cases, the systems and techniques described herein advantageously may be less expensive and complex than systems and techniques that employ fluoroscopy, and do not require exposing the patient to ionizing radiation. In addition, the systems and techniques described herein advantageously may enable more accurate determination of the position of the distal end of the elongate body than systems and techniques that employ visible markings on a proximal end of an elongate body, thereby better enabling a clinician to avoid unintended contact between the elongate body and the pericardium or other non-target tissues of the patient.

Figure 1B:
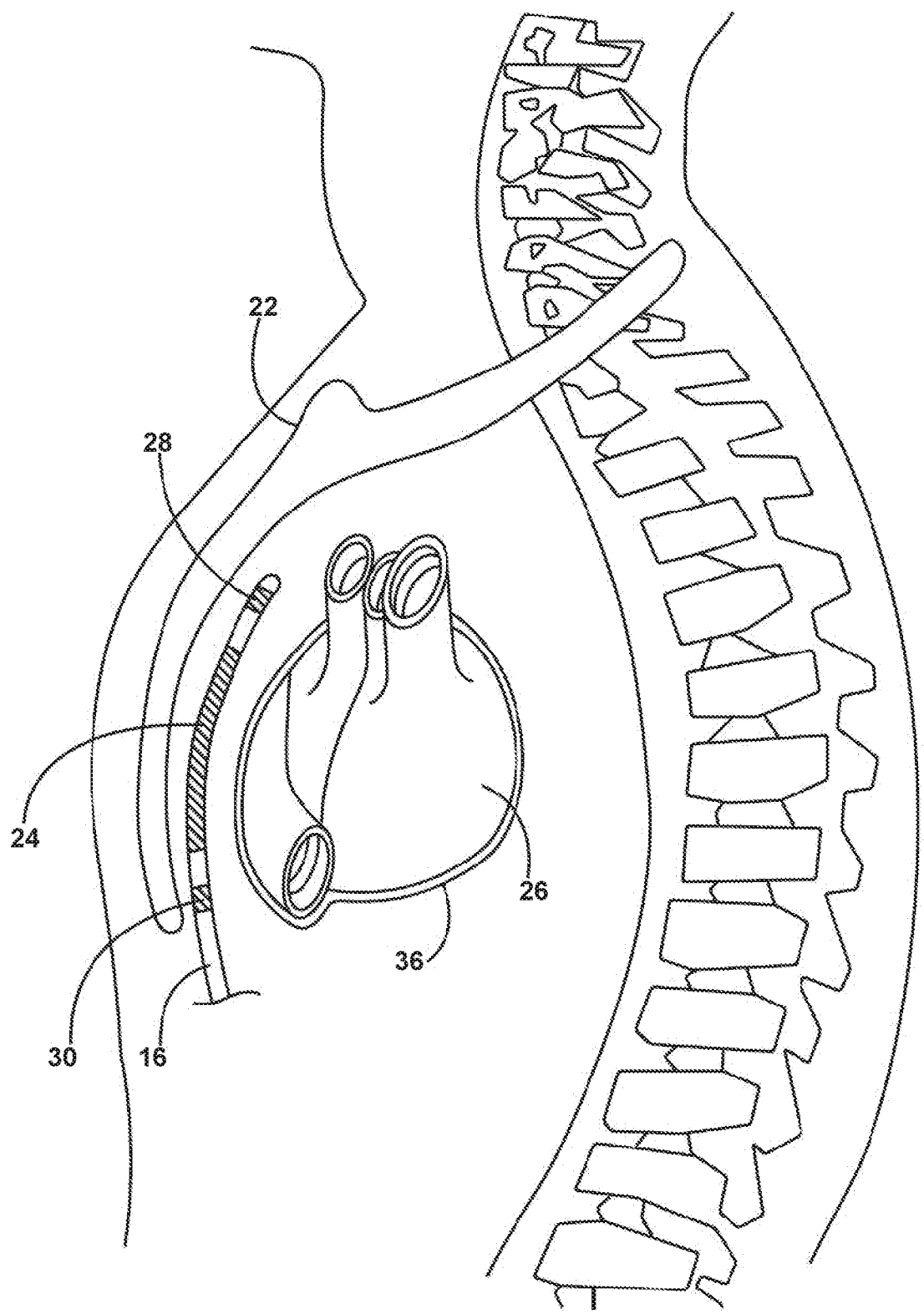
FIG. 1B is a conceptual drawing illustrating a side view of the patient implanted with the example implantable cardiac system of FIG. 1A.
Figure 1C:
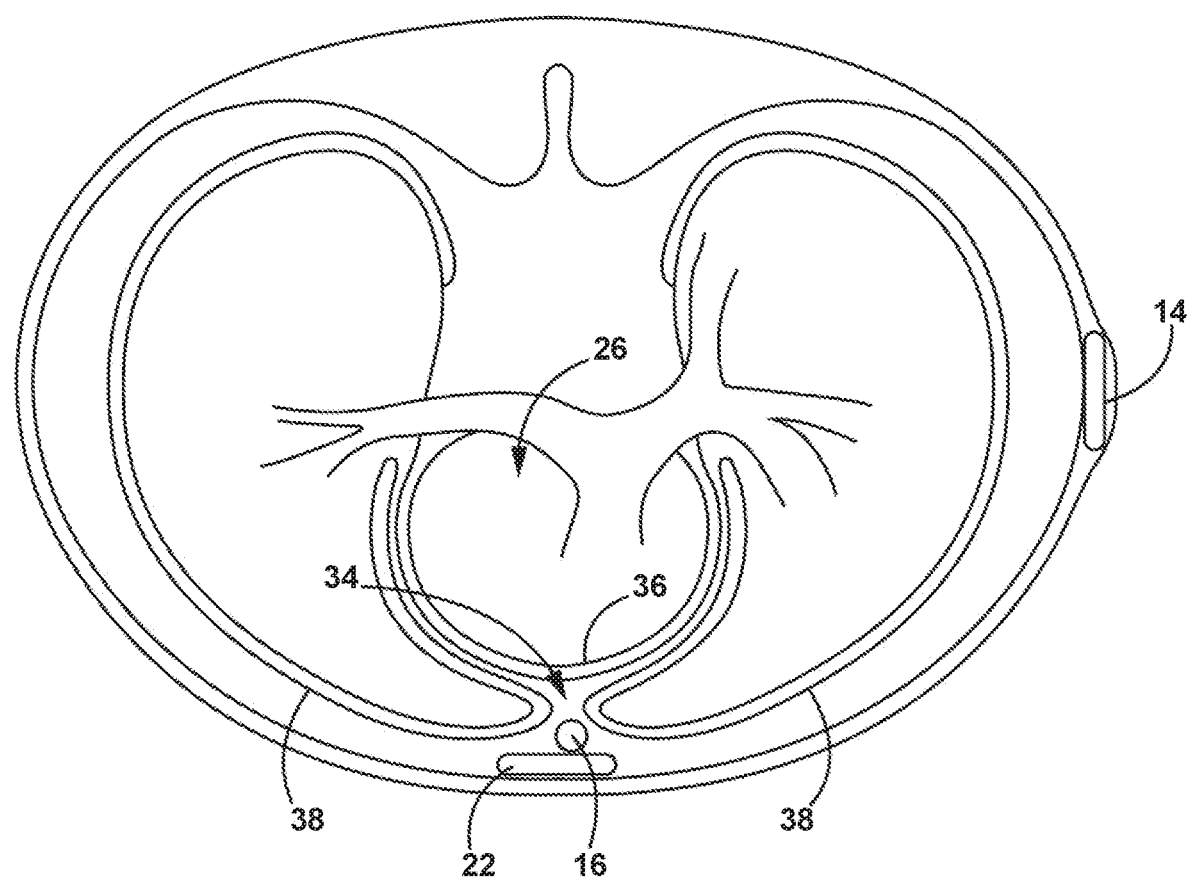
FIG. 1C is a conceptual drawing illustrating a transverse view of the patient implanted with the example implantable cardiac system of FIG. 1A.

FIGS. 1A-1C are conceptual diagrams of an extravascular ICD system 10 implanted within a patient 12. FIG. 1A is a front view of ICD system 10 implanted within patient 12. FIG. 1B is a side view of ICD system 10 implanted within patient 12. FIG. 1C is a transverse view of ICD system 10 implanted within patient 12.

ICD system 10 includes an ICD 14 connected to a medical electrical lead 16. FIGS. 1A-1C describe an implantable medical system capable of providing defibrillation and/or cardioversion shocks and, in some examples, pacing pulses. However, the techniques of this disclosure may also be used for implanting implantable medical leads, systems or devices configured to provide other electrical stimulation therapies to the heart or other organs, nerves, tissue or muscles (e.g., neurostimulators), or leads, catheters, devices or systems to provide other therapies (e.g., drug therapies).

ICD 14 may include a housing that forms a hermetic seal that protects components of ICD 14. The housing of ICD 14 may be formed of a conductive material, such as titanium, or of a combination of conductive and non-conductive materials. The conductive material of the housing functions as a housing electrode. ICD 14 may also include a connector assembly (also referred to as a connector block or header) that includes electrical feedthroughs through which electrical connections are made between lead 16 and electronic components included within the housing. The housing may house one or more of processing circuitry, memories, transmitters, receivers, sensors, sensing circuitry, therapy circuitry, power sources and other appropriate components.

ICD 14 is configured to be implanted in a patient, such as patient 12. ICD 14 is implanted subcutaneously on the left midaxillary of patient 12. ICD 14 is on the left side of patient 12 above the ribcage. ICD 14 may, in some examples, be implanted between the left posterior axillary line and the left anterior axillary line of patient 12. ICD 14 may, however, be implanted at other subcutaneous locations on patient 12 such as at a pectoral location or abdominal location.

Lead 16 includes an elongated lead body having a proximal end that includes a connector (not shown) configured to be connected to ICD 14 and a distal portion that includes electrodes 24, 28, and 30. The implant tools and techniques of this disclosure may be used to implant lead 16 as described herein (or implant other types of leads, catheters, devices, or other implantable components). Lead 16 extends subcutaneously above the ribcage from ICD 14 toward a center of the torso of patient 12, e.g., toward xiphoid process 20 of patient 12. At a location near the center of the torso, lead 16 bends or turns and extends intrathoracically superior under/below sternum 22. In one example, lead 16 may extend intrathoracically superior under/below sternum 22 within anterior mediastinum 34. Anterior mediastinum 34 may be viewed as being bounded posteriorly by pericardium 36, laterally by pleurae 38, and anteriorly by sternum 22. In some examples, the anterior wall of anterior mediastinum 34 may also be formed by the transversus thoracis and one or more costal cartilages. Anterior mediastinum 34 includes a quantity of loose connective tissue (such as areolar tissue), some lymph vessels, lymph glands, substernal musculature (e.g., transverse thoracic muscle), and small vessels or vessel branches. In one example, the distal portion of lead 16 may be implanted substantially within the loose connective tissue and/or substernal musculature of anterior mediastinum 34. A lead implanted substantially within anterior mediastinum 34 will be referred to herein as a substernal lead. Also, electrical stimulation, such as pacing, cardioversion or defibrillation, provided by lead 16 implanted substantially within anterior mediastinum 34 may be referred to herein as substernal electrical stimulation, substernal pacing, impedance monitoring, substernal cardioversion, or substernal defibrillation.

The distal portion of lead 16 is described herein as being implanted substantially within anterior mediastinum 34. Thus, points along the distal portion of lead 16 may extend out of anterior mediastinum 34, but the majority of the distal portion is within anterior mediastinum 34. In other embodiments, the distal portion of lead 16 may be implanted intrathoracically in other non-vascular, extra-pericardial locations, including the gap, tissue, or other anatomical features around the perimeter of and adjacent to, but not attached to, the pericardium or other portion of heart 26 and not above sternum 22 or ribcage. As such, lead 16 may be implanted anywhere within the "substernal space" defined by the undersurface between the sternum and/or ribcage and the body cavity but not including the pericardium or other portion of heart 26. The sub sternal space may alternatively be referred to by the terms "retrosternal space" or "mediastinum" or "infrasternal" as is known to those skilled in the art and includes the anterior mediastinum 34. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, the distal portion of lead 16 may be implanted in the region around the outer surface of heart 26, but not attached to heart 26.

The distal portion of lead 16 may be implanted substantially within anterior mediastinum 34 such that electrodes 24, 28, and 30 are located near a ventricle of heart 26. For instance, lead 16 may be implanted within anterior mediastinum 34 such that electrode 24 is located over a cardiac silhouette of one or both ventricles as observed via an anterior-posterior (AP) fluoroscopic view of heart 26. In one example, lead 16 may be implanted such that a therapy vector from electrode 24 to a housing electrode of ICD 14 is substantially across the ventricles of heart 26. The therapy vector may be viewed as a line that extends from a point on electrode 24, e.g., center of electrode 24, to a point on the housing electrode of ICD 14, e.g., center of the housing electrode. However, lead 16 may be positioned at other locations as long as the therapy vector between electrode 24 and the housing electrode is capable of defibrillating heart 26.

In the example illustrated in FIGS. 1A-1C, lead 16 is located substantially centered under sternum 22. In other examples, however, lead 16 may be implanted such that it is offset laterally from the center of sternum 22. In some examples, lead 16 may extend laterally enough such that all or a portion of lead 16 is underneath/below the ribcage in addition to or instead of sternum 22. Further, although primarily described in the context of examples in which a distal portion of lead 16 is implanted within the anterior mediastinum and implantation within the plural or pericardial cavities is avoided, in some examples the distal portion of lead may be implanted in a pleural cavity or pericardial cavity of patient 12.

The elongated lead body of lead 16 contains one or more elongated electrical conductors (not illustrated) that extend within the lead body from the connector at the proximal lead end to electrodes 24, 28, and 30 located along the distal portion of lead 16. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some examples. However, lead bodies of less than 3 Fr and more than 9 Fr may also be utilized. In another example, the distal portion and/or other portions of the lead body may have a flat, ribbon or paddle shape. In this instance, the width across the flat portion of the flat, ribbon or paddle shape may be between 1 and 3.5 mm. Other lead body designs may be used without departing from the scope of this disclosure. The lead body of lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 16 may engage with respective ones of electrodes 24, 28, and 30. In one example, each of electrodes 24, 28, and 30 is electrically coupled to a respective conductor within the lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, and 30 and transmit sensed electrical signals from one or more of electrodes 24, 28, and 30 to the sensing module within ICD 14.

Defibrillation electrode 24 is illustrated in FIG. 1 as being an elongated coil electrode. Defibrillation electrode 24 may vary in length depending on a number of variables. Defibrillation electrode 24 may, in one example, have a length between about 5 centimeters (cm) to about 10 cm. However, defibrillation electrode 24 may have a length less than 5 cm and greater than 10 cm in other embodiments. Another example, defibrillation electrode 24 may have a length between about 2 cm to about 16 cm.

In other embodiments, however, defibrillation electrode 24 may be a flat ribbon electrode, paddle electrode, braided or woven electrode, mesh electrode, segmented electrode, directional electrode, patch electrode or other type of electrode besides an elongated coil electrode. In one example, defibrillation electrode 24 may be formed of a first segment and a second segment separated by a distance and having an electrode or a pair of electrodes (such as electrode 28 and/or 30 described below) located between the first and second defibrillation electrode segments. In one example, the segments may be coupled to the same conductor within the lead body such that the first and second segments function as a single defibrillation electrode. In other embodiments, defibrillation lead 16 may include more than one defibrillation electrode. For example, the first and second segments described above may be coupled to different conductors within the lead body such that the first and second segments function as separate defibrillation electrodes along the distal portion of lead 16. As another example, defibrillation lead 16 may include a second defibrillation electrode (e.g., second elongated coil electrode) near a proximal end of lead 16 or near a middle portion of lead 16.

Lead 16 also includes electrodes 28 and 30 located along the distal portion of lead 16. In the example illustrated in FIGS. 1A-1C, electrode 28 and 30 are separated from one another by defibrillation electrode 24. In other examples, however, electrodes 28 and 30 may be both distal of defibrillation electrode 24 or both proximal of defibrillation electrode 24. In examples in which defibrillation electrode 24 is a segmented electrode with two defibrillation segments, electrodes 28 and 30 may be located between the two segments. Alternatively, one of electrodes 28 and 30 may be located between the two segments with the other electrode located proximal or distal to defibrillation electrode 24. Electrodes 28 and 30 may comprise ring electrodes, short coil electrodes, hemispherical electrodes, segmented electrodes, directional electrodes, or the like. Electrodes 28 and 30 of lead 16 may have substantially the same outer diameter as the lead body. In one example, electrodes 28 and 30 may have surface areas between 1.6-55 mm$^2$. Electrodes 28 and 30 may, in some examples, have relatively the same surface area or different surface areas. Depending on the configuration of lead 16, electrodes 28 and 30 may be spaced apart by the length of defibrillation electrode 24 plus some insulated length on each side of defibrillation electrode, e.g., approximately 2-16 cm. In other examples, such as when electrodes 28 and 30 are between a segmented defibrillation electrode, the electrode spacing may be smaller, e.g., less than 2 cm or less the 1 cm. The example dimensions provided above are exemplary in nature and should not be considered limiting of the embodiments described herein. In other examples, lead 16 may include a single pace/sense electrode or more than two pace/sense electrodes.

In some examples, electrodes 28 and 30 of lead 16 may be shaped, oriented, designed or otherwise configured to reduce extracardiac stimulation. For example, electrodes 28 and 30 of lead 16 may be shaped, oriented, designed or otherwise configured to focus, direct or point electrodes 28 and 30 toward heart 26. In this manner, pacing pulses delivered via lead 16 are directed toward heart 26 and not outward toward skeletal muscle. For example, electrodes 28 and 30 of lead 16 may be partially coated or masked with a polymer (e.g., polyurethane) or another coating material (e.g., tantalum pentoxide) on one side or in different regions so as to direct the pacing signal toward heart 26 and not outward toward skeletal muscle.

ICD 14 may obtain sensed electrical signals corresponding with electrical activity of heart 26 via a combination of sensing vectors that include combinations of electrodes 28 and/or 30 and the housing electrode of ICD 14. For example, ICD 14 may obtain electrical signals sensed using a sensing vector between electrodes 28 and 30, obtain electrical signals sensed using a sensing vector between electrode 28 and the conductive housing electrode of ICD 14, obtain electrical signals sensed using a sensing vector between electrode 30 and the conductive housing electrode of ICD 14, or a combination thereof. In some examples, ICD 14 may even obtain sensed electrical signals using a sensing vector that includes defibrillation electrode 24.

ICD 14 analyzes the sensed electrical signals obtained from one or more of the sensing vectors of lead 16 to monitor for tachyarrhythmia, such as ventricular tachycardia (VT) or ventricular fibrillation (VF). ICD 14 generates and delivers substernal electrical stimulation therapy, e.g., ATP, cardioversion or defibrillation shocks, and/or post-shock pacing in response to detecting tachycardia (e.g., VT or VF). In some examples, ICD 14 may generate and deliver bradycardia pacing in addition to ATP, cardioversion or defibrillation shocks, and/or post-shock pacing.

In the example illustrated in FIG. 1, system 10 is an ICD system that provides cardioversion/defibrillation and/or pacing therapy. However, the implant tools and techniques may be utilized to implant other types of implantable medical leads, catheters (e.g., drug delivery catheters), or other implantable component or assembly. In addition, it should be noted that system 10 may not be limited to treatment of a human patient. In alternative examples, ICD system 10 may be implemented in non-human patients, e.g., primates, canines, equines, pigs, ovines, bovines, and felines. These other animals may undergo clinical or research therapies that may benefit from the subject matter of this disclosure.

Figure 2:
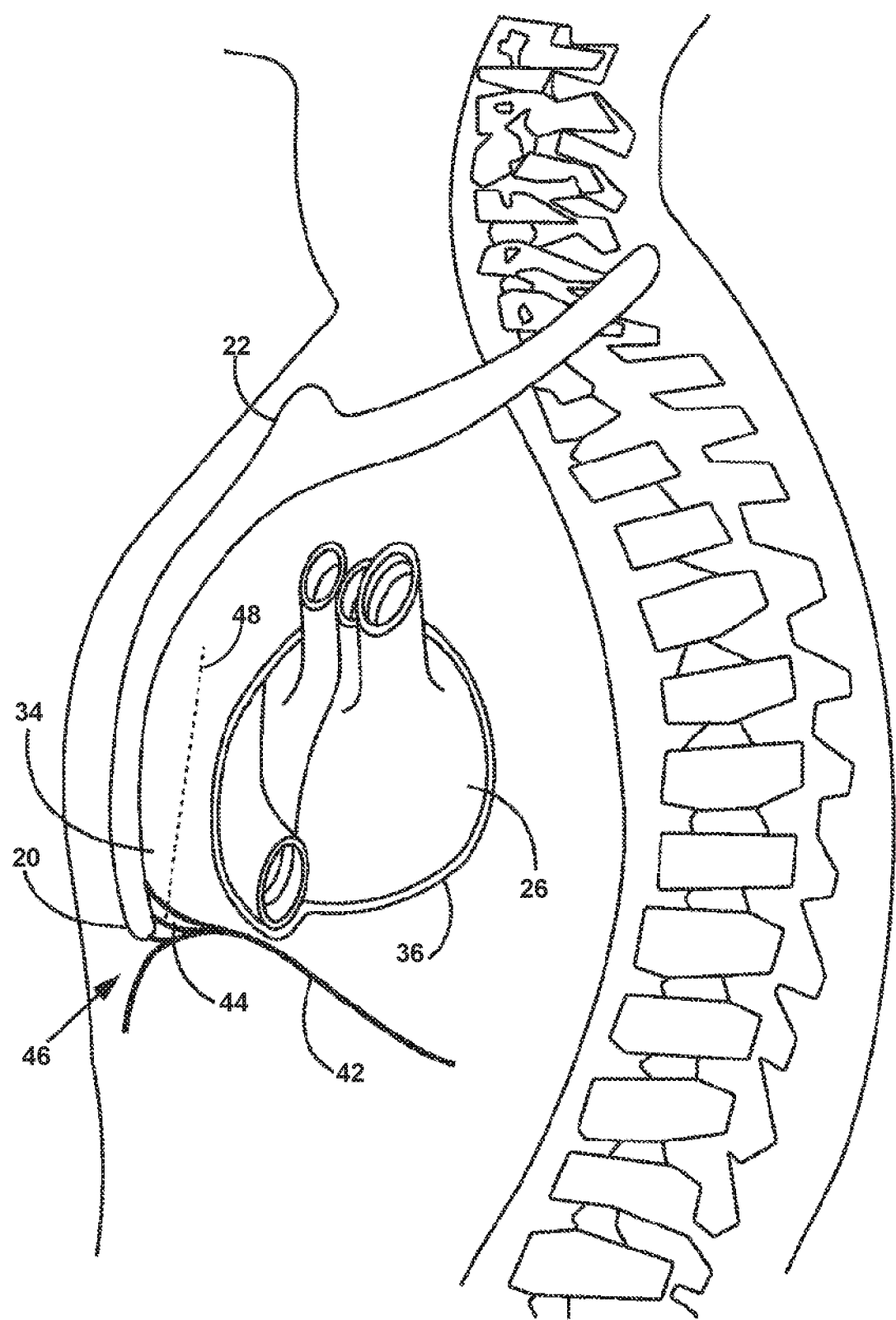
FIG. 2 is a conceptual drawing illustrating a side view of the patient showing tissue layers in and near a substernal space of the patient.

FIG. 2 is a conceptual drawing illustrating a side view of patient 12 showing tissue layers in and near a substernal space of patient 12. In the example of FIG. 2, diaphragm 42 and diaphragmatic attachments 44 are illustrated as being positioned inferior to anterior mediastinum 34. Diaphragmatic attachments 44 may be layers, sheets or other structures of fibrous tissue that function to connect diaphragm 42 to xiphoid process 20 of sternum 22. In the illustrated example, three layers of diaphragmatic attachments 44 are present in patient 12. In some other examples, such as in non-human species or in human patients having different anatomy, a larger or smaller number of layers of diaphragmatic attachments 44 may be present. Access site 46 is an access site in the skin of patient 12 for introducing implant tool or one or more other medical devices. As shown in FIG. 2, access site 46 may be positioned inferior to xiphoid process 20 and anterior of diaphragm 42, such as in the skin of the thorax of patient 12.

During a medical procedure to advance an elongate body of an implant tool (e.g., any of implant tools discussed below with respect to FIGS. 3-4C) a clinician may create a superficial incision at access site 46 and introduce the elongate body of the implant tool through the incision. The clinician then may create a passageway through diaphragmatic attachments 44 and into anterior mediastinum 34 with an elongate body of an implant tool. As discussed below in further detail, the implant tools described herein may include a pressure sensor, e.g., positioned within a lumen of an elongate body of the implant tool or a lumen of a fluid line of the implant tool, which may enable a system including the implant tool to determine when the distal end of the implant tool has crossed one or more of diaphragmatic attachments 44.

For example, as the clinician advances the elongate body through the diaphragmatic attachments 44, a pressure of fluid within the lumen of the elongate body and/or the implant tool may increase as a distal end of the elongate body contacts a first layer of diaphragmatic attachments 44, and then may decrease as the clinician advances the distal end of the elongate body past the first layer of the diaphragmatic attachments 44. Processing circuitry of a system including the implant tool may determine that such a decrease in the pressure of the fluid has occurred and provide an indication to the clinician, via a user interface, that the distal end of the implant tool has crossed the first layer of diaphragmatic attachments 44. The clinician then may advance the distal end of the elongate body through a final layer of diaphragmatic attachments 44. When the distal end of the elongate body crosses the final layer of diaphragmatic attachments 44, a segment of a signal corresponding to the pressure of the fluid may decrease again, and may include one or more amplitude oscillations indicative of respiratory function of patient 12. Based on this decrease in pressure and the appearance of amplitude oscillations, e.g., amplitude oscillations greater than a threshold amplitude, processing circuitry of the system then may provide an indication to the clinician that the distal end of the elongate body has crossed each of the layers of diaphragmatic attachments 44 and entered anterior mediastinum 34.

Based on the indication that the distal end of the implant tool has crossed each of diaphragmatic attachments 44, the clinician may manipulate the implant tool to change a direction of the elongate body. For example, the clinician may introduce a shaping member into a lumen of the elongate body, which may cause the elongate body to bend into a non-linear shape such that the distal end of the elongate body points in a substantially anterior direction within anterior mediastinum 34. The clinician then may advance the elongate body below sternum 22 within anterior mediastinum 34 (e.g. along line 48 of FIG. 2) to create a substernal tunnel. The clinician then may withdraw the elongate body from the tunnel. In some examples in which the implant tool includes a sheath configured to be positioned around the elongate body during creation of the substernal tunnel, the clinician may allow the sheath to remain within the substernal tunnel after the elongate body is withdrawn. After the elongate body has been withdrawn from patient 12, the clinician then may introduce a medical lead, such as lead 16 of FIGS. 1A-1C, into access site 46 and through the substernal tunnel along line 48 within anterior mediastinum 34.

Figure 3:
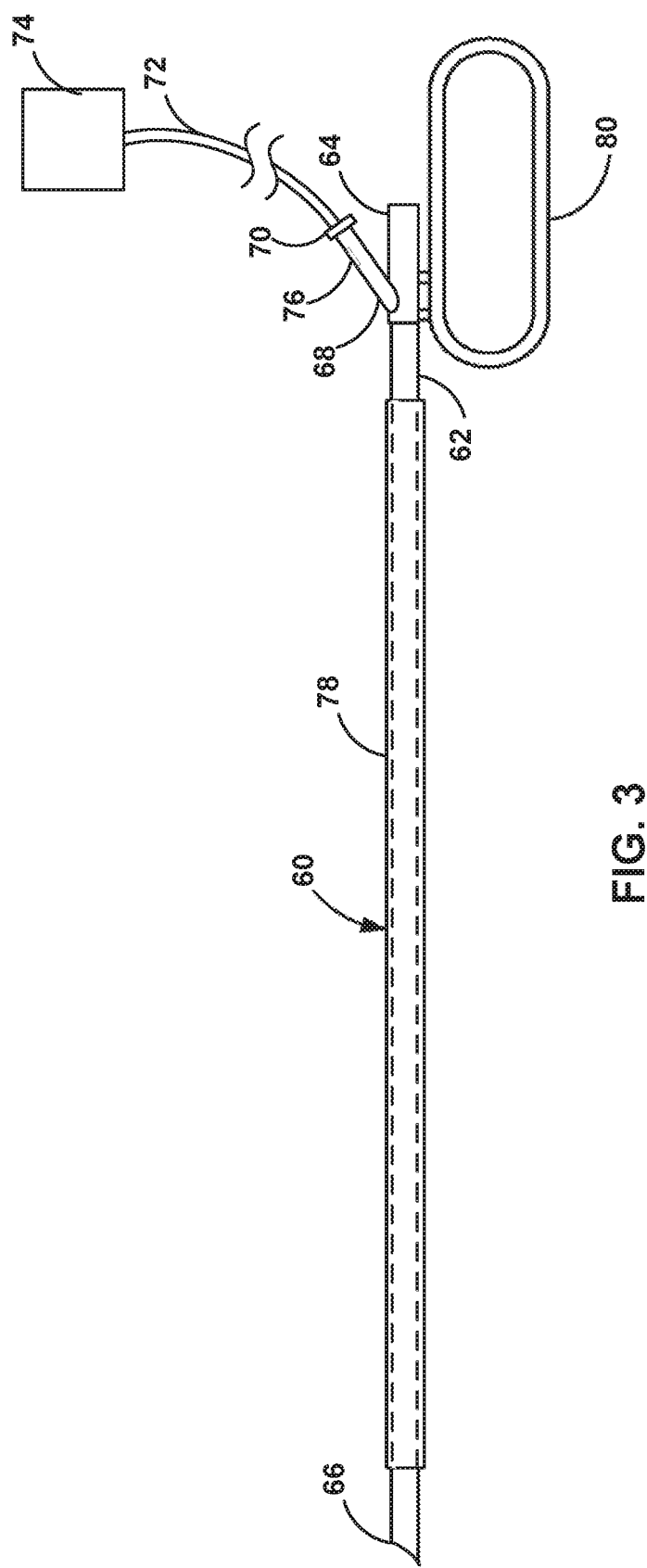
FIG. 3 is a side view of an example implant tool configured to access the substernal space of the patient during a technique of implanting the substernal lead of the implantable cardiac system of FIG. 1A.

FIG. 3 is a side view of a needle implant tool 60, which is configured to access the substernal space of patient 12 during a technique for implanting lead 16 of ICD 14 within anterior mediastinum 34 of patient 12. In the example shown in FIG. 3, needle implant tool 60 may comprise elongate body 62 that includes proximal end 64, distal end 66, and hub 68. Needle implant tool 60 may further comprise fluid port 70 and fluid line 72. Fluid line 72 may be in fluid communication with elongate body 62 via fluid port 70, and may be configured to supply a fluid (e.g., saline or another surgical irrigation solution) to elongate body 62 from fluid source 74. In the illustrated example, pressure sensor 76 may be positioned within hub 68. In other examples, pressure sensor may be positioned within a lumen (not shown) defined by elongate body 62 and/or fluid line 72. In any such examples, pressure sensor 76 may be positioned within a path of fluid flow between fluid source 74 and distal end 66, such that pressure sensor 76 is positioned to sense a pressure of fluid within needle implant tool 60.

In still other examples, pressure sensor 76 may be positioned on distal end 66 of elongate body 62. In such other examples, pressure sensor 76 may be configured to sense a tissue fluid pressure at the distal end 66 or mechanical resistance experienced by distal end 66 when distal end 66 encounters tissue such as diaphragmatic attachments 44 instead of being configured to sense a fluid pressure within a lumen of elongate body 62 or fluid line 72. For example, the pressure sensor 76 may be a pressure sensor capsule, e.g., including a capacitive pressure sensor, configured to sense both the drops in pressure and oscillations in an amplitude of a pressure signal that may indicate a position of distal end 66 of elongate body 62 relative to diaphragmatic attachments 44. Needle implant tool may further comprise sheath 78, which may be configured to be positioned around elongate body 62 during a medical procedure to advance elongate body 62 through diaphragmatic attachments 44 of patient 12, and handle 80, which may be any size and shape suitable for grasping by a clinician.

In some examples, elongate body 62 may be dimensioned for use during a procedure to implant a medical lead (e.g., lead 16) within anterior mediastinum 34 of patient 12. For example, a length of elongate body 62 from proximal end 64 to distal end 66 may be approximately 1 cm to approximately 25 cm, which may correspond to an approximate distance between access site 46 (shown in FIG. 2) and a lead placement site within anterior mediastinum 34, such as along line 48, or along a line substantially parallel with line 48 but closer to sternum 22 (not shown). In some examples, elongate body 62 may be malleable, which may allow a clinician to make adjustments to the configuration of elongate body 62, such as to adapt elongate body 62 to the anatomy of a specific patient. In some examples, elongate body 62 may be approximately 7 cm or longer to enable entry into the thoracic cavity and creation of a pathway for another tool. In some examples, elongate body 62 may have an outer diameter similar to a diameter of lead 16, such as from approximately 3 Fr to approximately 9 Fr. Thus, in some such examples, a procedure to advance elongate body 62 to a lead placement site within anterior mediastinum 34 may result in a substernal tunnel dimensioned to receive lead 16. Sheath 78 may have a diameter greater than the diameters of elongate body 62 and lead 16, such that a lumen defined by sheath 78 (not shown) may be sized to receive either elongate body 62 or lead 16. As further discussed below with respect to FIG. 10, lead 16 may be advanced through sheath 78 during a procedure for implanting lead 16 in anterior mediastinum 34.

Elongate body 62 may be formed, at least in part, of a biocompatible metal, such as stainless steel or a suitable polymer (e.g., polycarbonate or polypropylene). As shown in FIG. 3, distal end 66 of elongate body 62 may include a sharp cutting tip configured to pierce tissue (e.g., skin or diaphragmatic attachments 44) of patient 12. As described above, elongate body 62 may, in some examples, define a lumen (not shown) that extends at least partially through elongate body 62 to distal end 66, such as through hub 68 to distal end 66. Such a lumen of elongate body 62 may be in fluid communication with fluid line 72, such that a fluid supplied to fluid line 72 from fluid source 74 may exit elongate body 62 at distal end 66 during a medical procedure to advance elongate body 62 through diaphragmatic attachments 44 of patient 12.

Pressure sensor 76 may positioned within a portion of a lumen of elongate body 62 between hub 68 and distal end 66, a portion of the lumen of elongate body 62 extending through hub 68, or a lumen of fluid line 72 and used to sense a pressure of a fluid therein during a medical procedure to advance elongate body 62 through diaphragmatic attachments 44 of patient 12. Pressure sensor 76 may be any suitably sized pressure sensor configured to sense fluid pressure. For example, pressure sensor 76 may be a piezoresistive pressure transducer that includes a membrane (e.g., a silicon membrane or wafer) having circuitry components such as Wheatstone bridge circuitry, although any suitable type of pressure sensor may be used.

Pressure sensor 76 may be configured to transmit signals corresponding to a pressure of a fluid within a portion of a lumen of elongate body 62 between hub 68 and distal end 66, a portion of a lumen of elongate body 62 extending through hub 68, or a lumen of fluid line 72 to processing circuitry (e.g., of another device) via a wireless connection or a wired connection. In some examples in which pressure sensor 76 is configured to wirelessly transmit such signals, pressure sensor 76 may include an integrated antenna configured to transmit or receive electromagnetic signals for communication. For example, an antenna of pressure sensor 76 may be configured to transmit signals corresponding to a pressure of a fluid within a portion of a lumen of elongate body 62 between hub 68 and distal end 66, a portion of a lumen of elongate body 62 extending through hub 68, or a lumen of fluid line 72 via inductive coupling, electromagnetic coupling, tissue conductance, Near Field Communication (NFC), Radio Frequency Identification (RFID), Bluetooth, WiFi, or other proprietary or non-proprietary wireless telemetry communication schemes. In some such examples, an antenna of pressure sensor 76 may be coupled to communication circuitry of pressure sensor 76, which may drive such an antenna to transmit signals associated with a pressure of a fluid to processing circuitry of another device as described below with respect to FIG. 5.

In other examples, pressure sensor 76 may be configured to transmit signals associated with a pressure of a fluid, via a wired connection, to processing circuitry of another device. For example, pressure sensor 76 may be connected to one or more wires positioned within a portion of a lumen of elongate body 62 between hub 68 and distal end 66, a portion of a lumen of elongate body 62 extending through hub 68, or a lumen of fluid line 72 and configured to transmit signals associated with a pressure of a fluid to processing circuitry of another device. In other such examples, pressure sensor 76 may be mounted on a pressure catheter that may house one or more wires configured to transmit signals associated with a pressure of a fluid to processing circuitry of another device, such as a Mikro-Cath™ pressure catheter available from Millar, Inc. or any other suitably configured pressure catheter.

In some examples, pressure sensor 76 and any associated wires and/or pressure catheter may be fixedly attached to a wall of a portion of a lumen of elongate body 62 between hub 68 and distal end 66, a wall of a portion of a lumen of elongate body 62 extending through hub 68, or a wall of a lumen of fluid line 72 via adhesives, welding, or any other suitable fixatives. In examples in which pressure sensor 76 is positioned on a pressure catheter, the pressure catheter may be fixedly attached to a wall of a portion of a lumen of elongate body 62 between hub 68 and distal end 66, a wall of a portion of a lumen of elongate body 62 extending through elongate body 92, a wall of a portion of a lumen of elongate body 62 extending through hub 68, or a wall of a lumen of fluid line 72 at multiple points along a length of the pressure catheter. In any such examples, fixed attachment of pressure sensor 76 to a wall of a portion of a lumen of elongate body 62 between hub 68 and distal end 66, a wall of a portion of a lumen of elongate body 62 extending through hub 68, or a wall of a lumen of fluid line 72 may help enable accurate pressure sensing, such as by reducing a possibility of motion artifacts in a pressure of the fluid caused by movement of pressure sensor 76 and/or a pressure catheter on which pressure sensor 76 may be mounted.

In any examples of needle implant tool 60, pressure sensor 76 may be sufficiently sensitive to changes in a pressure of fluid within a portion of a lumen of elongate body 62 between hub 68 and distal end 66, a portion of a lumen of elongate body 62 within hub 68, and/or a lumen of fluid line 72 associated with drops in fluid pressure that occur as a clinician advances distal end 66 of elongate body 62 past each layer of diaphragmatic attachments 44, as well as to oscillations in fluid pressure that occur as the clinician advances distal end 66 of elongate body 62 past a deepest layer of diaphragmatic attachments 44 and into anterior mediastinum 34. For example, pressure sensor 76 may be sensitive changes in fluid pressure as small as approximately 0.1 Torr, even as fluid pressure is relatively high, such as approximately 100 Torr. In addition, in any examples of needle implant tool 60, pressure sensor 76 may be configured to transmit, to processing circuitry of another device, a signal corresponding to a pressure of a fluid within a lumen of elongate body 62, a lumen of hub 68, and/or a lumen of fluid line 72 at each of a plurality of time points during a medical procedure to advance elongate body 62 through diaphragmatic attachments 44.

Figure 4A:
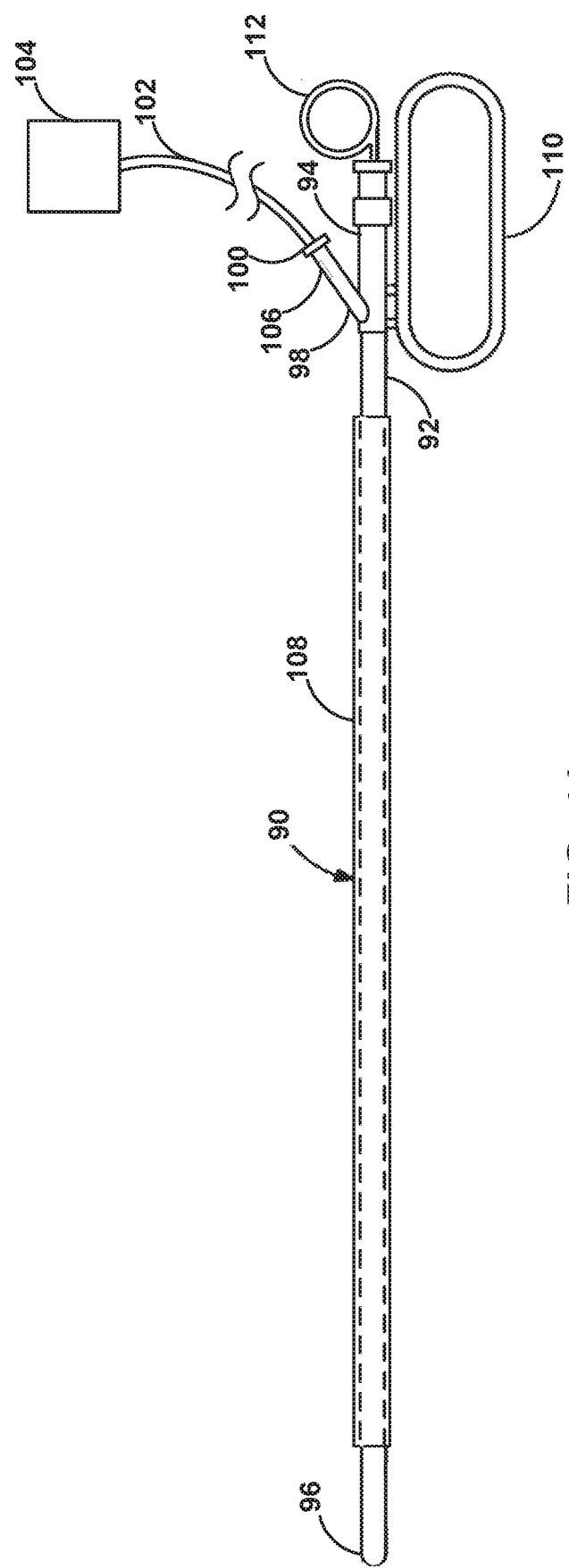
FIG. 4A is a side view of another example implant tool configured to access the substernal space of the patient during a technique of implanting the substernal lead of the implantable cardiac system of FIG. 1A.
Figure 4B:
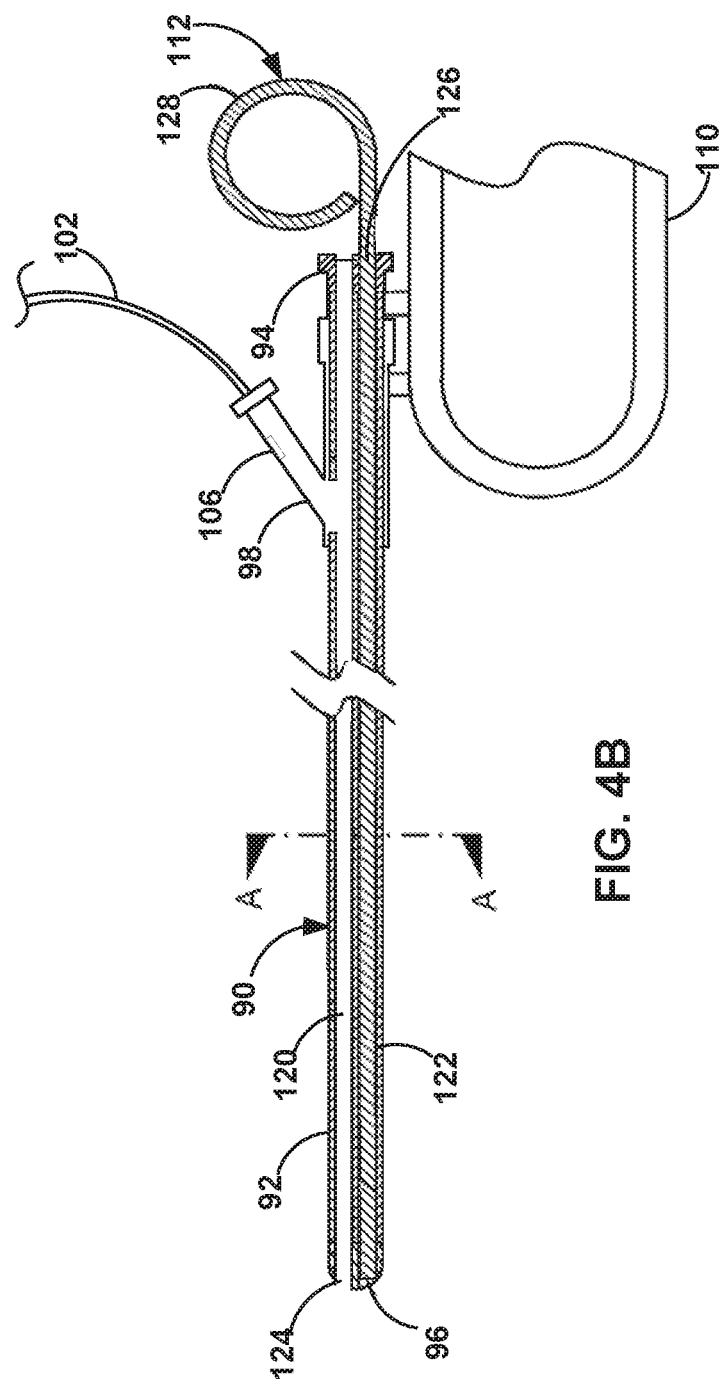
FIG. 4B is a partial-cross sectional side view of the example implant tool of FIG. 4A.
Figure 4C:
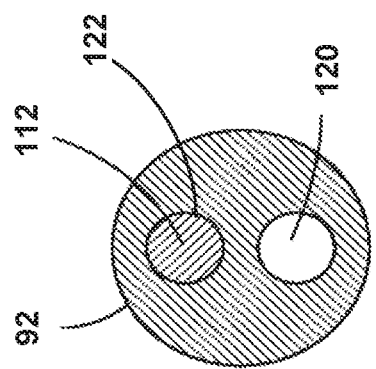
FIG. 4C is a cross-sectional view of the example implant tool of FIG. 4A, where the cross-section is taken along line A-A of FIG. 4B.

FIGS. 4A-4C illustrate blunt implant tool 90, which is configured to access the substernal space of patient 12 during a technique of implanting lead 16 of ICD 14. FIG. 4A is a side view of blunt implant tool 90. In the illustrated example, one or more features of the blunt implant tool 90 of FIGS. 4A-4C may be substantially similar to the corresponding features of the needle implant tool 60 described above with respect to FIG. 3, and will not be discussed again in detail here. For example, blunt implant tool 90 may include an elongate body 92 having a proximal end 94, a distal end 96, and a hub 98 that may be substantially similar to hub 68. Similar to elongate body 62 of needle implant tool 60, elongate body 92 of blunt implant tool 90 may be dimensioned for using during a procedure to implant a medical lead (e.g., lead 16) within anterior mediastinum 34 of patient 12. In the example of FIGS. 4A-4C, blunt implant tool 90 also includes fluid port 100, fluid line 102, fluid source 104, pressure sensor 106, sheath 108, and handle 110, which may be substantially similar in configuration and function to respective ones of fluid port 70, fluid line 72, fluid source 74, pressure sensor 76, sheath 78, and handle 80 of needle implant tool 60 as described with respect to FIG. 3.

Blunt implant tool 90 may differ from needle implant tool 60 in one or more of a shape of distal end 96, a material composition of elongate body 92, and an optional additional feature of a shaping member 112. For example, distal end 96 may be blunt and configured for blunt tissue dissection during a medical procedure to advance elongate body 92 through diaphragmatic attachments 44. Elongate body 92 may be formed of any metal or polymer or combination thereof. For example, elongate body 92 may be formed of rigid material such as a biocompatible metal (e.g., stainless steel) or a rigid polymer. In another example, elongate body 92 may be formed of a thermoplastic polymer, such as polyether block amide (PEBA), high-density polyethylene (HDPE), or any other suitable polymer or biocompatible metal or alloy (e.g., Nitinol) that may provide elongate body 92 with sufficient flexibility to assume one or more non-linear shapes when the optional shaping member 112 is inserted into a lumen of elongate body 92, as discussed below with respect to FIGS. 4B and 4C. In some examples, a proximal portion of elongate body 92 that includes proximal end 94 may be substantially inflexible, and a distal portion of elongate body 92 that includes distal end 96 may be flexible. For example, the proximal portion of elongate body 92 that includes proximal end 94 may be composed of a rigid material, such as a substantially inflexible polymer or metal (e.g., stainless steel) and the distal portion of elongate body 92 that includes distal end 96 may be formed of the aforementioned flexible materials. In some such examples, the proximal portion of elongate body 92 that includes proximal end 94 may be joined to the distal portion of elongate body 92 that includes distal end 96 at approximately a midpoint of a length of elongate body 92, although the two portions may be adjoined at other locations along the length of elongate body 92.

FIG. 4B is a partial-cross sectional side view of blunt implant tool 90. As shown in FIG. 4B, elongate body 92 may define a fluid lumen 120 and an optional shaping member lumen 122. Each of fluid lumen 120 and shaping member lumen 122 may extend at least partially through elongate body 92 to distal end 96. As shown in FIG. 4B, fluid lumen 120 may extend through hub 98, such that fluid lumen 120 is in fluid communication with hub 98 and a lumen (not shown) of fluid line 102. In some examples, fluid lumen 120 may extend from distal opening 124 at distal end 96 of elongate body 92 to proximal end 94 of elongate body 92 and may be closed by proximal end 94 of elongate body 92. In some other examples, fluid lumen 120 may extend from distal opening 124 at distal end 96 of elongate body 92 to a point distal to proximal end 94.

In still other examples, instead of distal opening 124, elongate body 92 may include a membrane positioned at distal end 96 and configured to deflect upon contact with diaphragmatic attachments 44. In such examples, pressure sensor 106 may sense changes in pressure of the fluid within fluid lumen 120 as the membrane deflects, which may occur when as the membrane contacts or crosses through diaphragmatic attachments 44, and exerts pressure on the fluid within fluid lumen 120. In some such examples, the fluid supplied by fluid source 104 to fluid lumen 120 may be any suitable gas or liquid to which the membrane positioned at distal end 96 is substantially impermeable, which may limit the volume of the fluid that may exit opening 124 of fluid lumen 120 and enter patient 12. For example, the fluid supplied by fluid source 104 to fluid lumen 120 may be an inert gas, which may be more easily sterilized at or around the time of manufacturing of blunt implant tool 90 than a liquid.

Shaping member lumen 122 may extend from a position proximal to distal end 96 of elongate body 92 to an opening 126 at proximal end 94 of elongate body 92 and may be closed by distal end 96 of elongate body 92. Shaping member lumen 122 may be configured to slidably receive shaping member 112, which a clinician may use to manipulate a shape of elongate body 92 during a medical procedure to implant lead 16. In some examples, shaping member 112 may formed of one or more malleable materials, such as a stainless-steel mandrel, metals or alloys containing aluminum, silver, iron, copper, tin, lithium, or indium, or any other suitable malleable materials that enable shaping member 112 to retain linear or non-linear shapes into which it may be manipulated by a clinician.

In some examples, shaping member 112 may be configured to be inserted into opening 126 at proximal end 94 of elongate body 92 and slide a length of shaping member lumen 122 substantially to distal end 96 of elongate body 92. In some examples, shaping member 112 may be sized to substantially fill the entire volume of shaping member lumen 122, such that a friction fit may be formed between shaping member 112 and an inner wall of elongate body 92 that defines shaping member lumen 122. In other examples, shaping member 112 may be sized to loosely fit within the shaping member lumen 122, such that shaping member 112 readily may be withdrawn from shaping member lumen 122. In still other examples, shaping member 112 may be fixed within shaping member lumen 122, such as by being molded or otherwise bonded within shaping member 112.

As shown in FIG. 4B, shaping member 112 may include a grip 128 positioned at a proximal end of shaping member 112 that extends proximally from opening 126 of proximal end 94 of elongate body 92 when shaping member 112 is received within shaping member lumen 122. In some examples, grip 128 may be ring-shaped, such that a clinician may pull on grip 128 with a single finger, although grip 128 may have any shape that may enable a clinician to easily grasp grip 128 during a medical procedure. In examples in which shaping member 112 is not fixed from shaping member lumen 122, a clinician may advance or withdraw shaping member 112 to or from a desired position within shaping member lumen 122 by pushing or pulling on grip 128, which may help enable the clinician to manipulate blunt implant tool 90 into a desired configuration.

One or more materials from which shaping member 112 is formed may be sufficiently malleable to enable a clinician to manipulate shaping member 112 from a first configuration into a second configuration and sufficient plasticity to enable shaping member 112 to retain the second configuration. The one or more materials from which shaping member may be formed also may have sufficient strength to enable shaping member 112 to retain elongate body 92 in a shape of a portion of shaping member 112 that is received within shaping member lumen 122. For example, during a portion of a medical procedure to implant lead 16 in which a clinician advances distal end 96 of elongate body 92 through diaphragmatic attachments 44 and into anterior mediastinum 34 of patient 12, shaping member 112 may be positioned in a substantially linear configuration within shaping member lumen 122, thereby retaining elongate body 92 in a substantially linear configuration. Upon advancing distal end 96 of elongate body 92 past diaphragmatic attachments 44 and into anterior mediastinum 34, a clinician may manipulate shaping member 112 into a non-linear (e.g., bent) configuration within shaping member lumen 122, such as by manipulating a distal portion of elongate body into which shaping member 112 extends within shaping member lumen 122. Such a non-linear configuration may enable the clinician to direct elongate body 92 in a superior direction toward a lead placement site within anterior mediastinum 34 during subsequent steps of the medical procedure, as further discussed with respect to FIG. 6.

FIG. 4C is a cross-sectional view of elongate body 92 of blunt implant tool 90, where the cross-section is taken along line A-A of FIG. 4B. In some examples, such as the example of FIG. 4C, fluid lumen 120 and shaping member lumen 122 each may be offset from a central longitudinal axis of elongate body 92. In other examples, one of fluid lumen 120 or shaping member lumen 122 may be coextensive with the central longitudinal axis of elongate body 92, and the other one of fluid lumen 120 and shaping member lumen 122 may be offset from the central longitudinal axis of elongate body 92. In other examples, blunt implant tool 90 may not include shaping member lumen 122 and shaping member 112.

Figure 5:
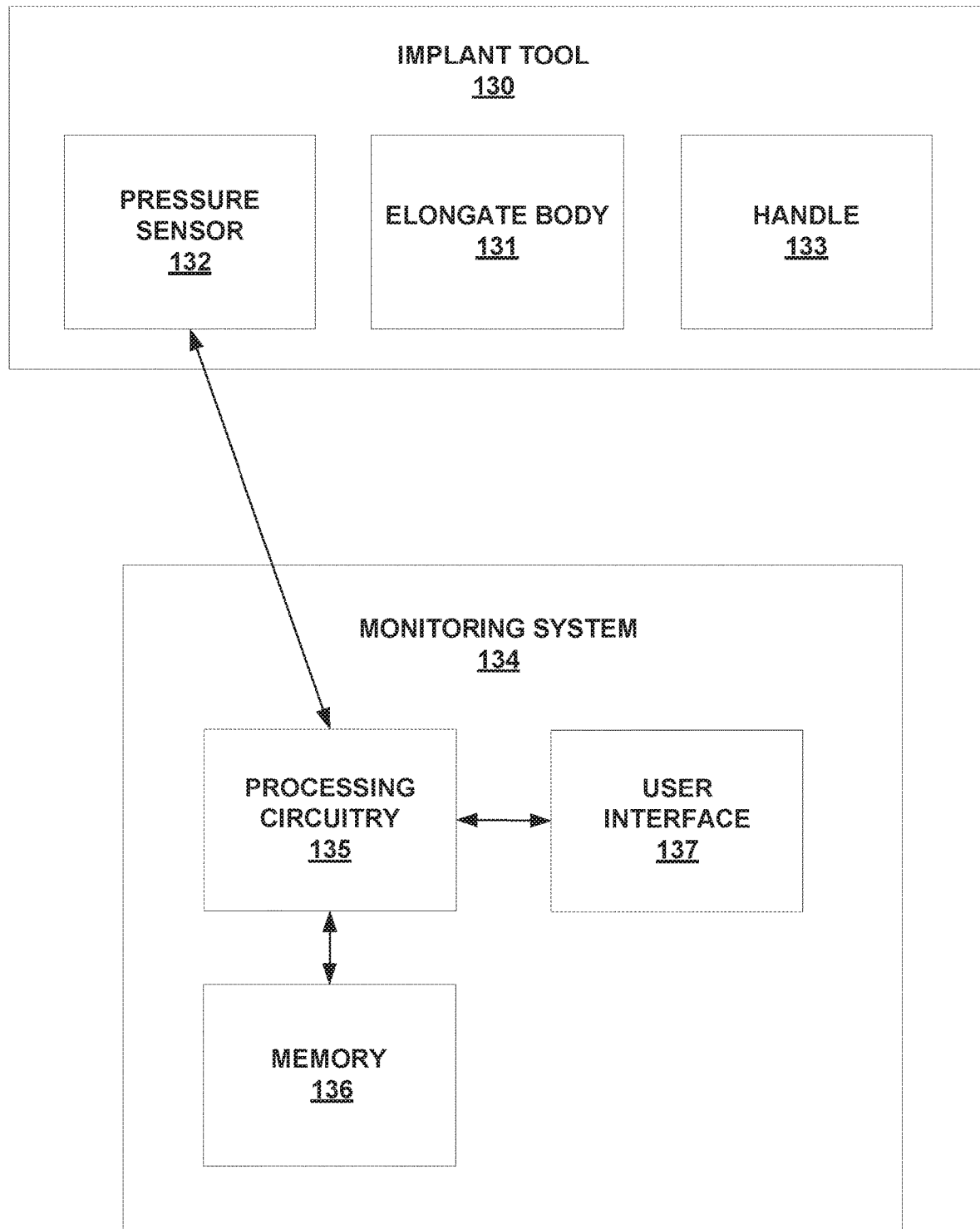
FIG. 5 is a functional block diagram illustrating an example configuration of an example implant tool and an example configuration of a monitoring system.

FIG. 5 is a functional block diagram illustrating an example configuration of implant tool 130 having elongate body 131, pressure sensor 132, and handle 133, and an example configuration of monitoring system 134. In some examples, implant tool 130 may be either needle implant tool 60 of FIG. 3 or blunt implant tool 90 of FIGS. 4A-4C. In some examples, monitoring system 134 generally may be a system configured to receive signals from a pressure sensor of implant tool 130 to determine a position of a distal end of elongate body 131, and transmit an indication of the position of distal end of elongate body 131 to a clinician during a medical procedure to advance elongate body 131 through diaphragmatic attachments 44. In the example of FIG. 5, monitoring system 134 includes processing circuitry 135, memory 136, and user interface 137. In some examples, memory 136 includes computer-readable instructions that, when executed by processing circuitry 135, cause processing circuitry 135 to perform various functions described herein. Memory 136 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, one or both of implant tool 130 and monitoring system 134 may include one or more additional components. For example, implant tool 130 may include processing circuitry configured to perform one or more of the functions described herein with respect to processing circuitry 135 of monitoring system 134. Additionally, or alternatively, one or both of implant tool 130 and monitoring system 134 may include communication circuitry including any suitable hardware, firmware, software or any combination thereof, which may enable wireless communication between implant tool 130 and monitoring system 134. For example, implant tool 130 may include communication circuitry configured to wirelessly transmit one or more signals corresponding to a pressure of a fluid within a fluid lumen of implant tool 130 sensed by a pressure sensor of implant tool 130 to processing circuitry 135.

Processing circuitry 135 may include fixed function circuitry and/or programmable processing circuitry. Processing circuitry 135 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 135 may include multiple components, such as any combination of one or more microprocessors, one or more controllers, one or more DSPs, one or more ASICs, or one or more FPGAs, as well as other discrete or integrated logic circuitry. The functions attributed to processing circuitry 135 herein may be embodied as software, firmware, hardware or any combination thereof.

In some examples, processing circuitry 135 also may include a rectifier, filter, amplifier (e.g., a sense amplifier), comparator, and/or analog-to-digital converter. Upon receiving, from a pressure sensor within implant tool 130, a signal corresponding to a pressure of a fluid within a fluid lumen of elongate body 131 at each of a plurality of time points during a medical procedure to advance elongate body 131 through diaphragmatic attachments 44, processing circuitry 135 may determine a position of a distal end of elongate body 131 relative to diaphragmatic attachments 44. For example, processing circuitry 135 may determine a difference between two amplitude values of the signal received from a pressure sensor of implant tool 130 and determine an amplitude oscillation status of a segment of the signal that includes two of the plurality of time points. Processing circuitry 135 then may determine the position of a distal end of elongate body 131 relative to diaphragmatic attachments 44, based on the difference between the two amplitude values and the amplitude oscillation status of the segment of the signal. In some examples, processing circuitry 135 may be configured to receive the signal corresponding to the pressure of fluid from the pressure sensor via a wired connection to the pressure sensor, such as a wired connection of a microcatheter or other wires associated with a pressure sensor as described above with respect to implant tool 60 of FIG. 3. In other examples, processing circuitry 135 may be configured to receive the signal corresponding to the pressure of the fluid from the pressure sensor via a wireless connection, such as via an antenna of the pressure sensor configured to transmit pressure signals via inductive coupling, electromagnetic coupling, tissue conductance, Near Field Communication (NFC), Radio Frequency Identification (RFID), Bluetooth, WiFi, or other proprietary or non-proprietary wireless telemetry communication schemes.

Upon determining the position of the distal end of elongate body 131 relative to diaphragmatic attachments 44, processing circuitry 135 then may control user interface 137 to provide an indication of the position of the distal end of elongate body 131, such as at each of a plurality of time points during a procedure to advance elongate body 92 through diaphragmatic attachments 44. Such time points may include a time point at which the distal end of elongate body 131 crosses a first layer of diaphragmatic attachments 44 and a time point at which the distal end of elongate body 131 crosses a third (e.g., final) layer of diaphragmatic attachments and enters anterior mediastinum 34. In some examples, processing circuitry 135 may cause user interface 137 to provide an indication of the position of the distal end of elongate body 131 when the distal end of elongate body 131 is within a certain distance of pericardium 36, such as based on a determination that an oscillation status of a segment of the signal includes oscillations associated with respiration of patient 12.

In some examples, user interface 137 may provide indications of a position of distal end 96 that may be one or more of audible, visible, or tactile in nature. Such positions may include a position superficial to all of diaphragmatic attachments 44, a position between diaphragmatic attachments 44, or a position deep to all of diaphragmatic attachments 44. In some examples, user interface 137 may produce a first number of audible tones (e.g., one) when the distal end of elongate body 131 crosses a first layer of diaphragmatic attachments 44 and a second number of audible tones (e.g., two) when the distal end of elongate body 131 crosses a second or other intermediate layer of diaphragmatic attachments 44. Regardless of the number of layers of diaphragmatic attachments 44, in such examples, user interface 137 may produce a third number of audible tones (e.g., three) when the distal end of elongate body 131 has entered anterior mediastinum 34. In examples in which two layers of diaphragmatic attachments 44 are present, user interface 137 may produce the third number of audible tones shortly after the second number of audible tones. In other examples, an audible indication may include a certain pitch or other audible feature that may be associated with a certain position of the distal end of elongate body 131. In other examples, user interface 137 may display a visible indication of the position of the distal end of elongate body 131 on a graphical user interface (GUI) of monitoring system 134, by activating one or more light sources (e.g., one or more LEDs) positioned on monitoring system 134, or by any other suitable visible indication. In still other examples, user interface 137 may produce a tactile indication of the position of the distal end of elongate body 131 relative to diaphragmatic attachments 44, such as by causing one or more portions of monitoring system 134 or implant tool 130 to vibrate. It should be understood that the aforementioned indications that may be provided by user interface 137 are exemplary in nature, and that user interface 137 may be configured to provide any other suitable indications of the position of the distal end of elongate body 131 to a clinician. In any such examples, user interface 137 may be configured to produce such audible, visible, or tactile indications in a preview mode when implant tool 130 is not being used so as to familiarize the clinician with the meanings of the audible, visible, or tactile indications.

The various components of implant tool 130 and monitoring system 134 may be coupled to one or more power sources, which may include one or more rechargeable or non-rechargeable batteries positioned on or within one or both of implant tool 130 and monitoring system 134. In some other examples, one or both of implant tool 130 and monitoring system 134 may be configured for a wired connection to a power source.

Figure 6:
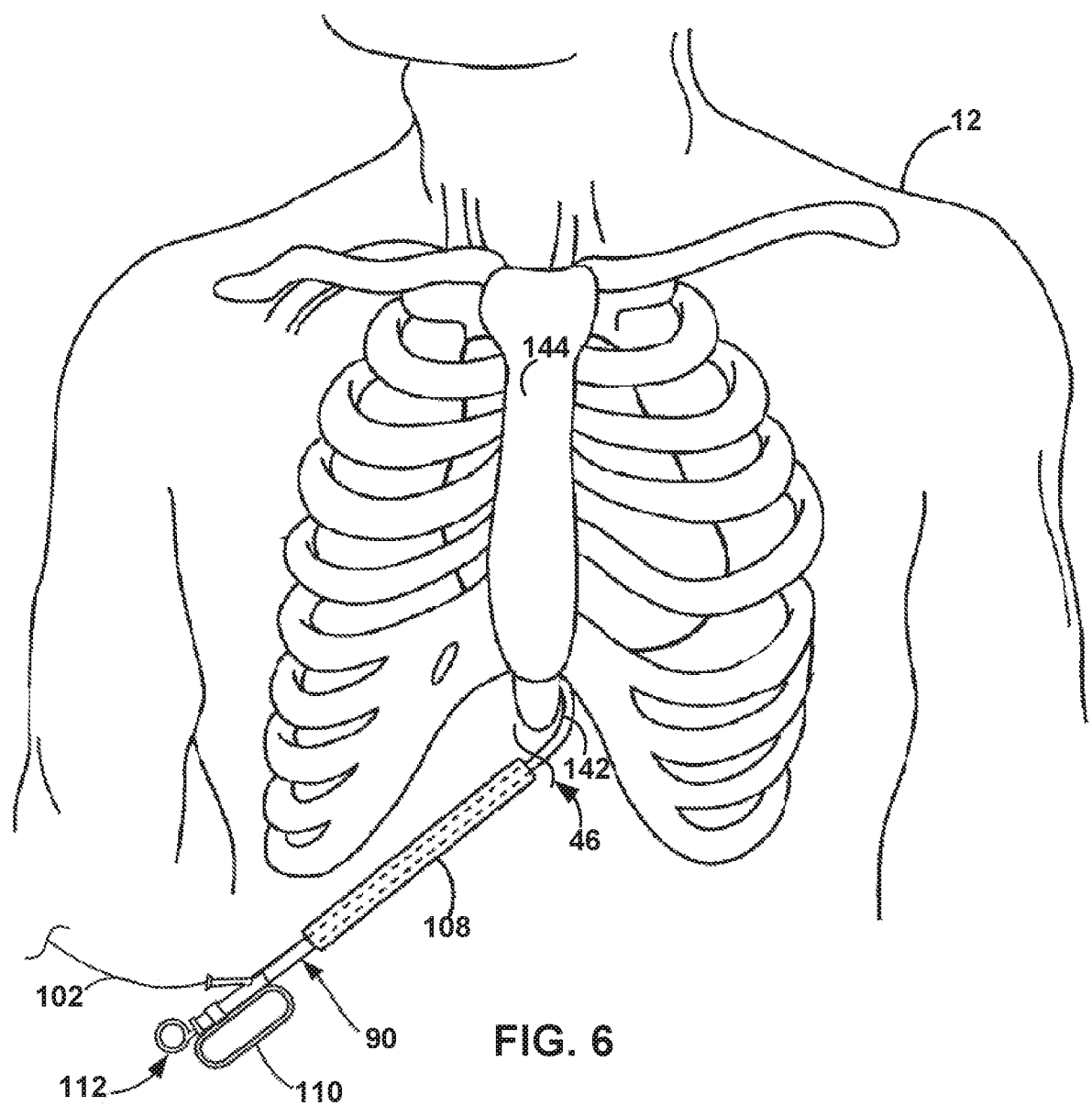
FIG. 6 is a conceptual drawing illustrating a front view of the patient with the example implant tool of FIG. 4A being inserted beneath the sternum of the patient during a technique of implanting the substernal lead of the implantable cardiac system of FIG. 1A.

FIG. 6 is a conceptual drawing illustrating a front view of patient 12 with blunt implant tool 90 of FIG. 4A being inserted beneath sternum 22 of patient 12 during a technique of implanting a lead (e.g., lead 16 of system 10) within anterior mediastinum 34. In the example of FIG. 6, distal end 96 of elongate body 92 has been advanced past diaphragmatic attachments 44 into anterior mediastinum 34 to a location between an inferior end of sternum 22 and lead placement site 144 At this point, a clinician may find it desirable to bend elongate body 92 into a shape a curve or bend, such as the radially upward bend at point 142 of elongate body 92 illustrated in FIG. 6, before the clinician continues to advance elongate body 92 within anterior mediastinum 34 toward lead placement site 144. For example, forming such a curve or bend in elongate body 92 may enable the clinician to advance elongate body 92 toward lead placement site 144 while maintaining distance between handle 110 and patient 12, even when proximal end 94 of elongate body 92 is advanced closer to access site 46. In some cases, it may be desirable to maintain a separation between handle 110 and patient 12 while advancing elongate body 92 toward lead placement site 144. For example, maintaining a separation between handle 110 may prevent handle 110 from interfering with the advancement of elongate body 92, which may help the clinician retain control over the direction of movement of elongate body 92 as elongate body is advanced toward lead placement site 144. Enabling the clinician to retain control over the direction of movement of elongate body 92 may reduce a likelihood of elongate body 92 moving in unintended directions, such as toward heart 26, during such procedures. As shown in FIG. 6, shaping member 112 is received within shaping member lumen 122 of elongate body 92, and elongate body 92 has been bent at point 142 to introduce a first curve into elongate body 92. Such a bent shape, or any other bent shape into which the clinician may manipulate elongate body 92, may have any suitable configuration, such as any configuration that may help the clinician control the direction of movement of elongate body 92.

In some examples, once the clinician has advanced distal end 96 of elongate body 92 to lead placement site 144, the clinician may withdraw elongate body 92 from sheath 108, leaving sheath 108 extending from access site 46 to lead placement site 144 along the path created by elongate body 92. The clinician then may advance lead 16 through sheath 108 to lead placement site 144 and withdraw sheath 108 from patient 12 via access site 46, leaving lead 16 in place at lead placement site 144. The clinician then may complete any additional steps of the medical procedure, such as implanting an IMD (e.g., ICD 14 of system 10) at a subcutaneous location within patient 12 and connecting lead 16 to ICD 14 of system 10.

Figure 7:
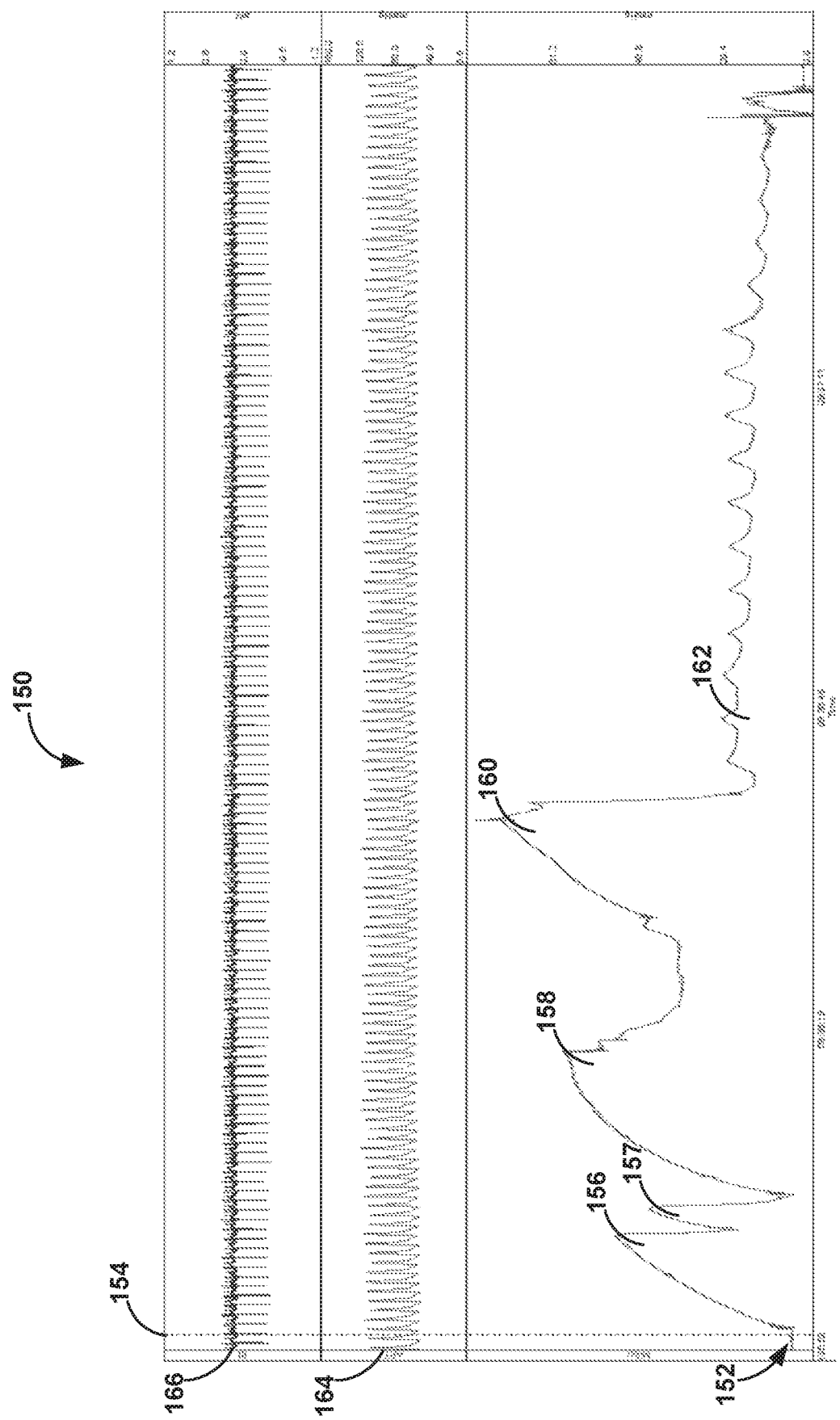
FIG. 7 is a graphical illustration of a pressure within the implant tool of FIG. 3, an ECG signal, and an arterial pressure observed during an example technique to create a path through diaphragmatic attachments of the porcine subject to a substernal space (e.g., an anterior mediastinum) of a porcine subject using the implant tool of FIG. 3.
Figure 8:
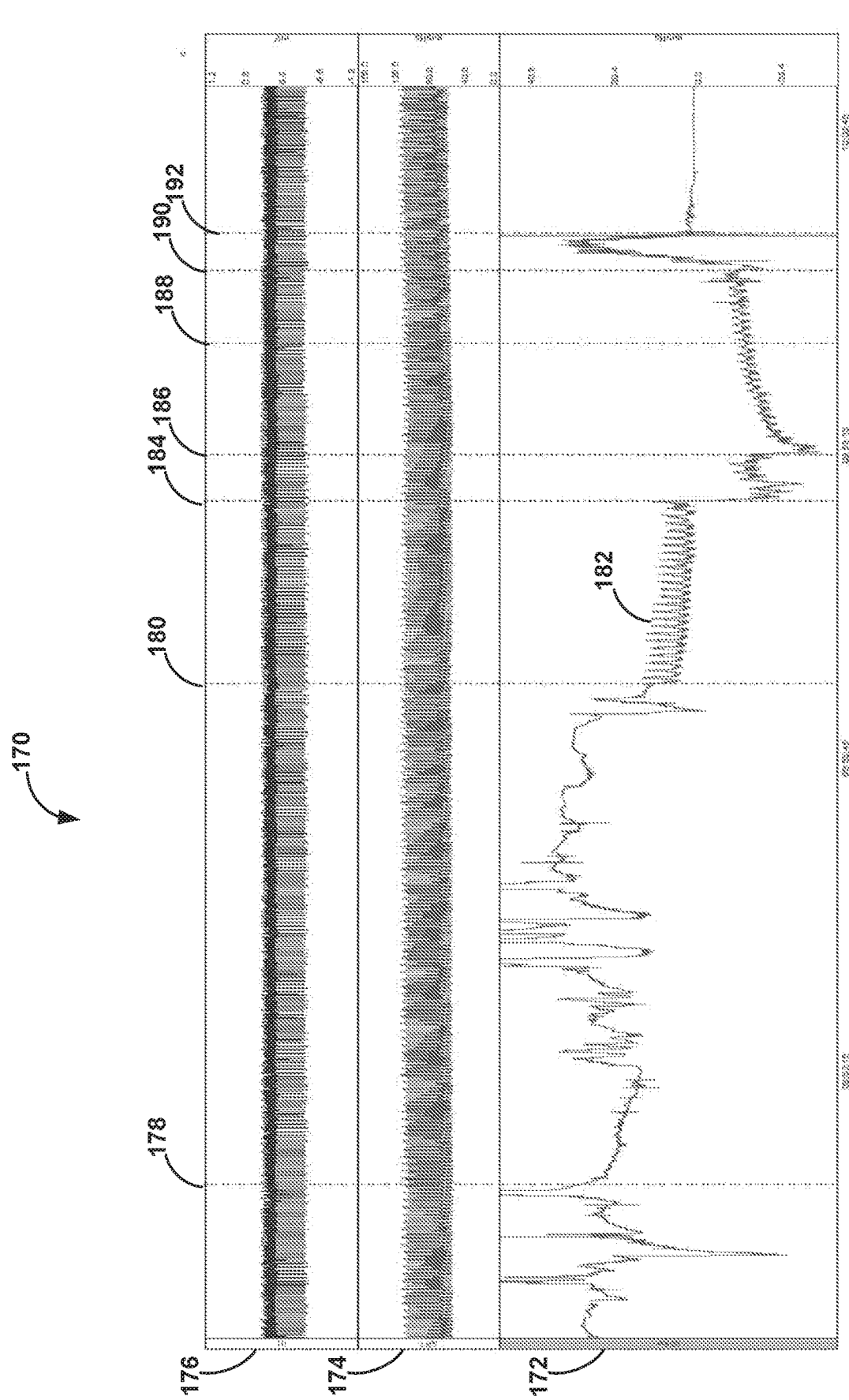
FIG. 8 is a graphical illustration of a pressure within the implant tool of FIG. 4A, an ECG signal, and an arterial pressure observed during an example technique to create a path through the substernal space of the porcine subject of FIG. 7 to a lead placement site using the implant tool of FIG. 4A.

FIGS. 7 and 8 are graphical illustrations of working examples of using the needle implant tools and blunt implant tools described herein, which show a pressure within the respective needle implant tool and blunt implant tool, an ECG signal, and an arterial pressure during example procedures carried out in a porcine subject to create a path into a substernal space (e.g., an anterior mediastinum) of the porcine subject. The needle implant tool used in the working example of FIG. 7 was substantially similar to needle implant tool 60 of FIG. 3, and the blunt implant tool used in the working example of FIG. 8 was substantially similar to blunt implant tool 90 of FIGS. 4A-4C. Thus, for the sake of clarity and reference, the working example of FIG. 7 is described in terms of needle implant tool 60 of FIG. 3, and the working example of FIG. 8 is described as using the blunt implant tool 90 of FIGS. 4A-4C. However, blunt implant tool 90 and needle implant tool 60 could have been used interchangeably in the working examples of FIGS. 7 and 8, with substantially similar pressure signal morphology as the pressure signal morphology illustrated in FIGS. 7 and 8 being expected to result. Although the working examples of FIGS. 7 and 8 are described with respect to results of the corresponding example procedures carried out in the porcine subject, such results may be substantially similar to results that may be observed during similar procedures carried out in patient 12. In addition, the anatomy and physiology of the porcine subject may be similar enough to the anatomy and physiology of patient 12 that the procedures corresponding to FIGS. 7 and 8 may be carried out in a substantially similar manner in patient 12.

FIG. 7 is a graphical illustration of a pressure within needle implant tool 60 of FIG. 3, an ECG signal, and an arterial pressure observed during an example procedure to create a path through diaphragmatic attachments of the porcine subject to a substernal space, such as an anterior mediastinum, of the porcine subject using needle implant tool 60. In some examples, user interface 137 of monitoring system 134 may be configured to provide a visual indication of the position of distal end 66 of elongate body 62 during a procedure to advance elongate body 62 through diaphragmatic attachments (e.g., porcine diaphragmatic attachments, which may be similar to diaphragmatic attachments 44) by displaying graphical user interface (GUI) 150. As shown in FIG. 7, GUI 150 may include pressure waveform 152. Pressure waveform 152 is an indication of a pressure of a fluid, in millimeters of mercury (mmHg), within a lumen of elongate body 62 and/or within fluid line 72 over time during such a procedure.

At time point 154, a clinician began to advance elongate body 62 into an access site of the subject. Pressure sensor 76 sensed the fluid pressure as the clinician advanced elongate body 62 and transmitted a signal associated with the pressure of the fluid to processing circuitry (e.g., processing circuitry 135 of monitoring system 134), which caused user interface 137 to display pressure waveform 152 via GUI 150. As the clinician continued to advance elongate body 62 toward the sub sternal space of the subject, distal end 66 of elongate body 62 encountered and crossed three layers of diaphragmatic attachments that correspond to peaks 156, 158, and 160 in pressure waveform 152 as the procedure progressed. Peak 156 corresponds to a most-superficial layer of the diaphragmatic attachments, peak 157 corresponds to a layer of the diaphragmatic attachments adjacent to and deep to the most-superficial layer of the diaphragmatic attachments, peak 158 corresponds to a middle layer of the diaphragmatic attachments, and peak 160 corresponds to a deepest layer of the diaphragmatic attachments. As distal end 66 of elongate body came into contact with each one of the layers of the diaphragmatic attachments, a fluid pressure within a lumen of elongate body 62 and/or within fluid line 72 increased due to mechanical resistance exerted on the fluid by each layer of the diaphragmatic attachments via an opening at distal end 66 of elongate body 62. As the clinician advanced elongate body 62 past the deepest layer of the diaphragmatic attachments, pressure sensor 76 sensed oscillations in the pressure of the fluid that correspond to amplitude oscillations 162 in pressure waveform 152. The appearance of amplitude oscillations 162 indicated that distal end 66 of elongate body 62 had crossed the deepest layer of the diaphragmatic attachments and entered the substernal space. After appearance of amplitude oscillations 162, the clinician withdrew elongate body 62 from sheath 78 and out of the subject via the access site, leaving behind sheath 78 positioned in the path created by elongate body 62 from the access site to the substernal space.

GUI 150 may further include additional waveforms, such as arterial pressure waveform 164 and/or ECG waveform 166. Arterial pressure waveform 164 and ECG waveform 166 respectively indicated arterial blood pressure and cardiac function of the porcine subject as the clinician advanced elongate body 62 from the access site to the substernal space. In some examples, it may be advantageous to monitor physiological parameters, such as arterial blood pressure and cardiac function, and display corresponding waveforms via GUI 150 during the medical procedures described herein. For example, significant changes in the waveforms corresponding to such physiological parameters may be indicative of adverse changes in patient condition during a medical procedure. For example, an inadvertent artery puncture caused by distal end 66 of elongate body 62 may result in a drop in arterial blood pressure. Thus, by observing arterial pressure waveform 164 and/or ECG waveform 166 via GUI 150, a clinician may quickly identify adverse changes in patient condition that may arise during the medical procedures described herein. In the example of FIG. 7, both arterial blood pressure and cardiac function of the porcine subject remained stable throughout the procedure depicted in FIG. 7, as indicated by arterial pressure waveform 164 and ECG waveform 166.

FIG. 8 is a graphical illustration of a pressure within blunt implant tool 90 of FIG. 4A, an ECG signal, and an arterial pressure observed during an example procedure to create a path through the substernal space of the porcine subject of FIG. 7 to a lead placement site using blunt implant tool 90 following the path created by elongate body 62 of needle implant tool 60 through the diaphragmatic attachments, as described with respect to FIG. 7. Some aspects of the example procedure illustrated in FIG. 8 are substantially similar to the example procedure illustrated in FIG. 7 and will not be discussed again in detail here. For example, graphical user interface (GUI) 170 includes pressure waveform 172, arterial pressure waveform 174, and ECG waveform 176, which correspond substantially to pressure waveform 152, arterial pressure waveform 164, and ECG waveform 166 of FIG. 7. The example procedure of FIG. 8 differs from the example procedure of FIG. 7 in that the procedure of FIG. 8 is a continuation of the procedure of FIG. 7.

At time point 178, shortly after the clinician began to advance elongate body 92, via sheath 78, through the path to the substernal space previously created by elongate body 62, elongate body 92 became stuck in a kink in sheath 78. The clinician then pulled the kinked portion of sheath 78 over distal end 96 of elongate body 92, which allowed the clinician to continue advancing elongate body 92 through the path created by elongate body 62. At time point 180, elongate body 92 reached the substernal space. The segment of pressure waveform 172 between time point 178 and time point 180 does not exhibit peaks indicative of resistance from the diaphragmatic attachments, as does pressure waveform 152 of FIG. 7, because elongate body 92 had followed the path through the diaphragmatic attachments that was created by elongate body 62. Fluctuations in the amplitude of pressure waveform 172 between time point 178 and time point 180 may be attributable to other factors, such as elongate body 92 becoming stuck in or otherwise coming into contact with sheath 78.

As elongate body 92 entered the substernal space, pressure sensor 106 sensed oscillations in the pressure of the fluid that correspond to amplitude oscillations 182 in pressure waveform 172, similarly to amplitude oscillations 162 in pressure waveform 152 of FIG. 7. Between time point 180 and time point 184, the clinician began to advance elongate body 92 through the substernal space in a superior direction toward a lead placement site beneath a superior portion of the subject's sternum, as pressure sensor 106 continued to sense oscillations in pressure corresponding to amplitude oscillations 182. At time point 184, elongate body 92 encountered a first substernal obstruction, which caused fluid within fluid lumen 120 of elongate body 92 to experience an increase in mechanical resistance between time point 184 and time point 186. Between time point 184 and time point 186, the clinician continued to advance elongate body 92 through or around the first obstruction in a superior direction toward the lead placement site. At time point 186, elongate body 92 crossed the first obstruction, which caused fluid within fluid lumen 120 of elongate body 92 to experience a decrease in mechanical resistance, as shown in a corresponding drop in amplitude of waveform 172 at time point 186.

As the clinician continued to advance elongate body 92 through the substernal space toward the lead placement site between time point 186 and time point 188, pressure sensor 106 continued to sense oscillations in the pressure of the fluid corresponding to amplitude oscillations 182 in pressure waveform 172. The amplitude of oscillations 182 between time point 186 and time point 188 is lower than the amplitude of oscillations 182 between time point 180 and time point 184 due to the presence of the first obstruction between distal end 96 of elongate body 92 and the subject's anterior mediastinum. That is, the presence of the first obstruction between distal end 96 and the subject's anterior mediastinum may dampen or attenuate oscillations 182 such that pressure sensor 106 detects oscillations 182 as having a lower amplitude between time point 186 and time point 188 than between time point 180 and time point 184. At time point 190, elongate body 92 encountered a second substernal obstruction, which caused fluid within fluid lumen 120 of elongate body 92 to experience an increase in mechanical resistance. Between time point 190 and time point 192, the clinician continued to advance elongate body 92 through the second obstruction in a superior direction toward the lead placement site. At time point 192, elongate body 92 crossed the first obstruction, which caused fluid within fluid lumen 120 of elongate body 92 to experience a decrease in mechanical resistance, as shown in a corresponding drop in amplitude of waveform 172 at time point 192. At time point 192, the clinician withdrew elongate body 92 from the subject, and disconnected a line (e.g., a catheter) of pressure sensor 106 from monitoring system 134.

Figure 9:
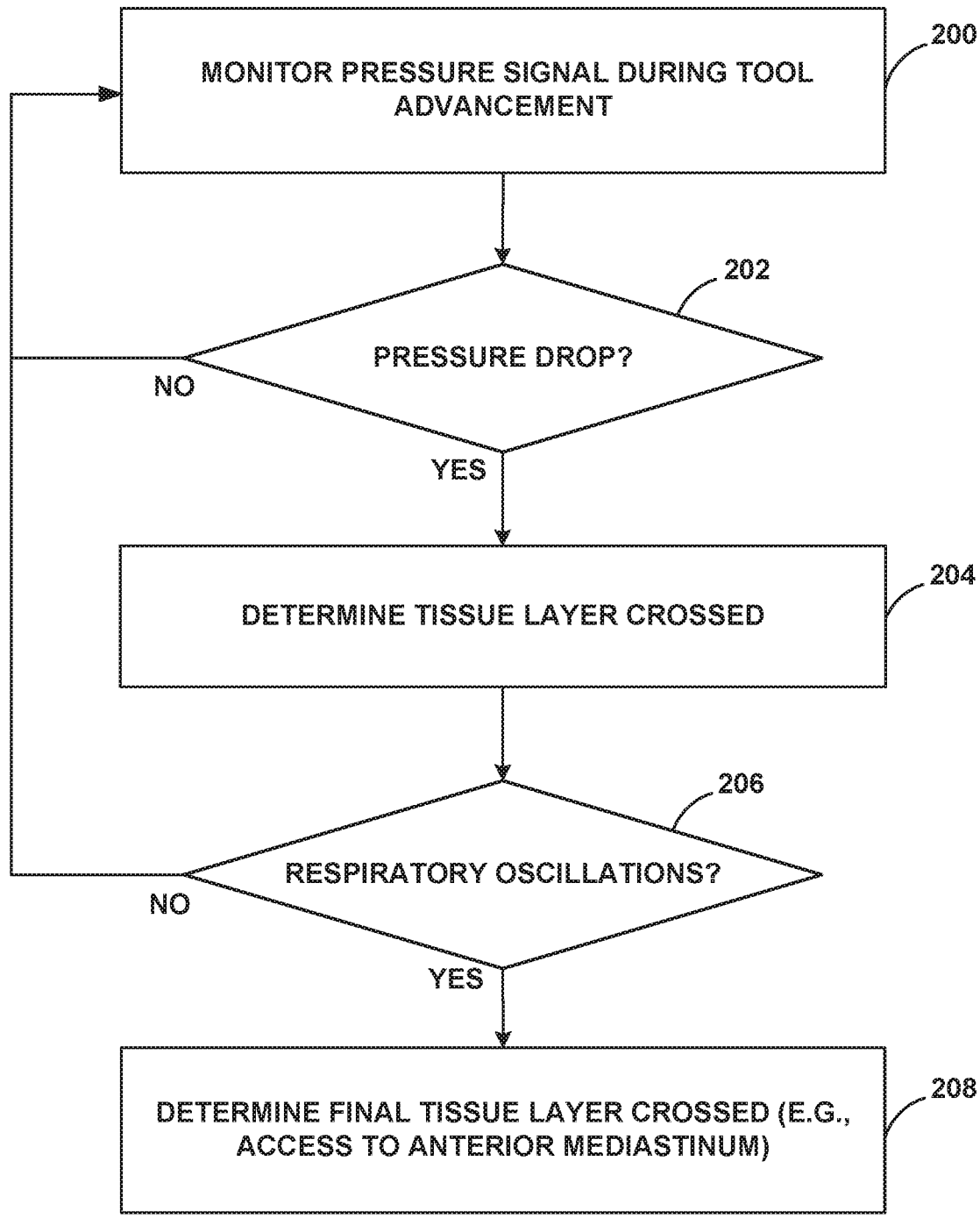
FIG. 9 is a flow chart illustrating an example technique for using the implant tool of FIGS. 3 and 4A to determine when the implant tool crosses through the tissue layers of FIG. 2.

In some examples, one or more aspects of the technique of FIG. 9 may be similar to one or more aspects of the example technique of FIG. 7. Although the processing circuitry 135 of monitoring system 134 is described as receiving or providing input at one or more steps of FIG. 9, processing circuitry of one or more other devices or systems may receive or provide such input in other examples. In the example technique of FIG. 9, a clinician may introduce a distal end of elongate body 131 into access site 46 of patient 12 and begin to advance elongate body 131 toward anterior mediastinum 34 while a fluid source introduces fluid into a lumen of a fluid line connected to elongate body 131. The fluid introduced into the fluid line flows into a fluid lumen defined by elongate body 131 via a hub positioned near a proximal end of elongate body 131, which may be substantially similar to hub 98 of blunt implant tool 90, and through the fluid lumen to a distal opening at the distal end of elongate body 131, where the fluid exits elongate body 131 and flows into tissue of patient 12. Pressure sensor 132 senses a pressure of the fluid as it flows past or through pressure sensor 132, and transmits a pressure signal corresponding to the pressure of the fluid to processing circuitry 135, which monitors the amplitude of the pressure signal over time (200). For example, as the distal end of elongate body 131 encounters a layer of diaphragmatic attachments 44, pressure sensor 132 senses an increase in the pressure of the fluid within the fluid lumen caused by the layer of diaphragmatic attachments 44 at least partially impeding the flow of fluid from the distal opening of elongate body 131. As the distal end of elongate body 131 crosses the layer of diaphragmatic attachments 44, the impediment to the flow of fluid from the distal opening is removed, and pressure sensor 132 senses a corresponding decrease in pressure of the fluid within the fluid lumen.

Processing circuitry 135 may monitor the amplitude to determine whether a drop in the amplitude of the pressure signal that corresponds to a drop in pressure exerted upon the fluid within the fluid lumen or a lumen of the fluid line has occurred (202). Such a drop in pressure may indicate that the distal end of elongate body 131 has been advanced past a layer of diaphragmatic attachments 44 of patient 12. In some examples, processing circuitry 135 may determine whether the drop in the amplitude of the pressure signal has occurred by determining a difference between two amplitude values of the signal received from pressure sensor 132 at two different time points of a plurality of time points of the pressure signal. If processing circuitry 135 determines that the difference between the two amplitude values is not indicative of a pressure drop that corresponds to the distal end of elongate body 131 crossing a layer of diaphragmatic attachments 44, processing circuitry 135 returns to monitoring the pressure signal during advancement of elongate body 131 to repeat step 200. In some examples, processing circuitry 135 may select the time points based on a timed (e.g., fixed) delay between a first time point and a subsequent time point, and/or may select the time points based on corresponding phases of respiratory or cardiac cycles of patient 12.

If processing circuitry 135 determines that the difference between the two amplitude values is indicative of such a pressure drop, processing circuitry 135 determines that the distal end of elongate body 131 has crossed the layer of diaphragmatic attachments 44 (204). In some examples, the difference between the two amplitude values that may be indicative of such a pressure drop may be a difference of about 5 Torr to about 20 Torr (i.e., about 667 Pa to about 2667 Pa). In some examples, processing circuitry 135 also may control user interface 137 to provide an indication of the position of the distal end of elongate body 131 as having crossed the layer of diaphragmatic attachments 44. Such an indication may be auditory, visible, tactile, or have any other suitable features, as described above with respect to FIG. 5.

Upon determining that the distal end of elongate body 131 has crossed the layer of diaphragmatic attachments 44, processing circuitry 135 evaluates the pressure signal to determine whether the pressure signal includes amplitude oscillations associated with respiration of patient 12 (206). In some examples, processing circuitry may determine that the distal end of elongate body has crossed one of diaphragmatic attachments 44 based on identifying a threshold number of amplitude oscillations associated with respiration of patient 12 (e.g., in cadence with breathing cycles of patient 12), such as two oscillations, three oscillations, or any other suitable threshold number. If processing circuitry determines that the pressure signal does not include such amplitude oscillations, processing circuitry 135 determines that additional ones of diaphragmatic attachments remain uncrossed by the distal end of elongate body 131 and returns to monitoring the pressure signal during advancement of elongate body 131 to repeat steps 200-204. If processing circuitry 135 determines that the pressure signal does include such amplitude oscillations, processing circuitry 135 determines that the distal end of elongate body 131 has crossed a final (e.g., deepest) layer of diaphragmatic attachments 44 (208), which may indicate that the distal end of elongate body 131 has entered anterior mediastinum 34. In some examples, processing circuitry 135 also may control user interface 137 to provide an indication of the position of distal end 96 as having crossed the final one of diaphragmatic attachments 44. Such an indication may be auditory, visible, tactile, or have any other suitable features, as described above with respect to FIG. 5.

In some examples, pressure sensor 132 continues to sense pressure and transmit a pressure signal after determining that the final tissue layer has been crossed. As discussed above, it may be desired to identify contact with sternum 22 after crossing the final layer of diaphragmatic attachments 44, e.g., to substantially maintain sternal contact and avoid contact with the heart or other unintended tissues while advancing the tool. In such examples, processing circuitry 135 may control user interface 137 to provide an indication indicating sternal contact. Processing circuitry 135 may, in some examples, identify sternal contact based on changes in the pressure after crossing the last tissue layer. In some examples, the change in the pressure signal that processing circuitry 135 may identify as being associated with sternal contact may depend on factors such as the design of pressure sensor 132, the orientation of pressure sensor 132, and/or the location of pressure sensor 132. For example, processing circuitry 135 may identify sternal contact based on a change in the pressure signal based on an increase or decrease in the amplitude of the pressure signal, (e.g., an amplitude of the pressure signal that satisfies a sternal contact pressure threshold. Additionally, or alternatively, processing circuitry 135 may identify sternal contact based on a reduction or absence of oscillations associated with respiration of patient 12.

Figure 10:
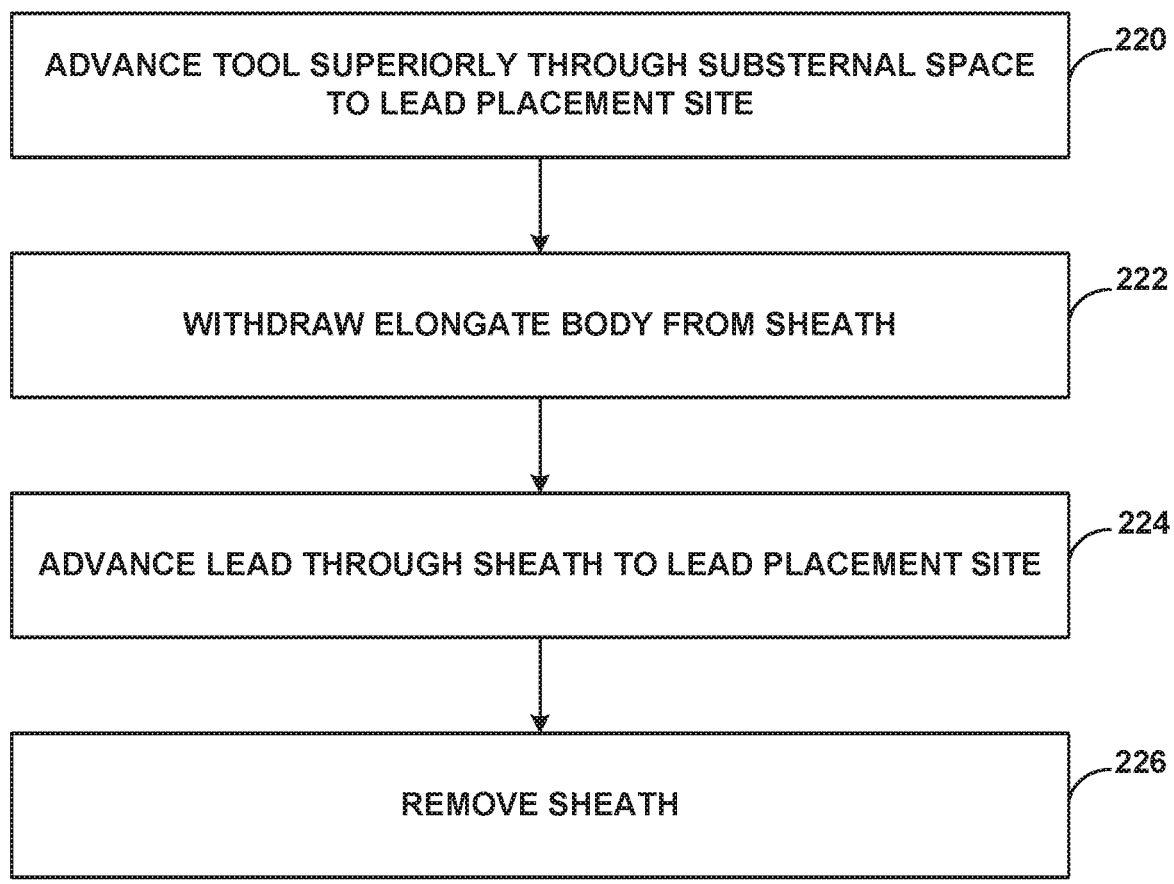
FIG. 10 is a flow chart illustrating an example technique for using the example implant tool of FIG. 4A to deliver the substernal lead of the implantable cardiac system of FIG. 1A to a lead placement site following the example technique of FIG. 8.

FIG. 10 is a flow chart illustrating an example technique for using needle implant tool 60 of FIG. 3, blunt implant tool 90 of FIG. 4A, or implant tool 130 of FIG. 5 to deliver lead 16 of ICD system 10 of FIG. 1A following the example technique of FIG. 9. In some examples, one or more aspects of the technique of FIG. 10 may be similar to one or more aspects of the example technique of FIG. 8. In the example technique of FIG. 10, the clinician may continue to advance elongate body 92, through the substernal space of patient 12 toward a lead placement site (e.g., lead placement site 144 of FIG. 6) (220). In some examples, pressure sensor 106 may continue to transmit pressure signals to processing circuitry 135 during the technique of FIG. 10, as described above with respect to FIG. 8. Once the clinician has advanced elongate body 92 through the substernal space of patient 12 to the lead placement site, the clinician may withdraw elongate body 92 from sheath 108, leaving sheath 108 extending from access site 46 to lead placement site 144 along the path created by elongate body 92 (222). The clinician then may advance lead 16 through sheath 108 to the lead placement site (224) and withdraw sheath 108 from patient 12 via access site 46, leaving lead 16 in place at the lead placement site (226). The clinician then may complete any additional steps of the medical procedure, such as implanting ICD 14 at a subcutaneous location within patient 12 and connecting lead 16 to ICD 14.

Figure 11:
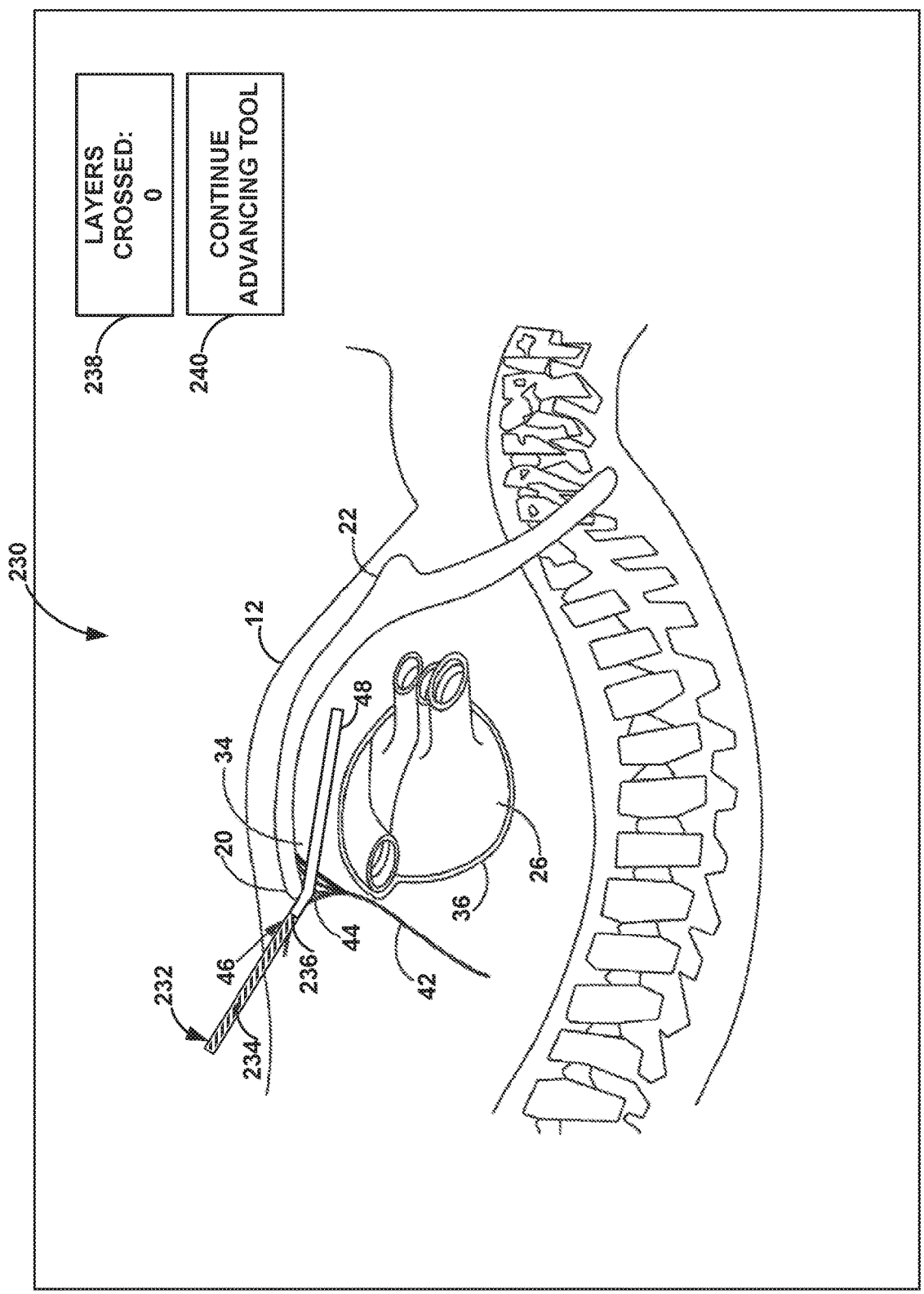
FIG. 11 is a conceptual drawing illustrating a graphical user interface displaying a representation of a side view of a thorax of a patient and a visible indication of a position of a distal end of the implant tool of FIGS. 3, 4A, and 5 relative to the tissue layers and sternum of FIG. 2.

FIG. 11 is a conceptual drawing illustrating a graphical user interface (GUI) 230 displaying a representation of a side view of a thorax of patient 12 and a progress bar 232 that includes a visible indication 234 of a position of distal end 66 of needle implant tool 60 of FIG. 3, distal end 96 of blunt implant tool 90 of FIG. 4A, or a distal end of implant tool 130 of FIG. 5 relative to diaphragmatic attachments 44 and sternum 22. Although GUI 230 is described below with respect to blunt implant tool 90, GUI 230 alternatively may be used with needle implant tool 60 or implant tool 130. In some examples, user interface 137 of monitoring system 134 may be configured to provide the visible indication of a position of distal end 96 elongate body 92 while advancing elongate body 92 through layers of diaphragmatic attachments 44 and beneath sternum 22 of patient 12 (e.g., according to the example techniques of FIG. 9 and/or FIG. 10) by displaying GUI 230. In some examples, monitoring system 134 may display GUI 230 in addition to or instead of a GUI including a pressure waveform, such as GUI 150 of FIG. 7 or GUI 170 of FIG. 8.

In the example of FIG. 11, progress bar 232 of GUI 230 may provide the clinician with a visible indication of the position of distal end 96 of elongate body 92 during a procedure to implant a medical lead (e.g., lead 16). As shown in FIG. 11, progress bar 232 may extend from a position exterior to patient 12 and along a planned path that elongate body 92 may travel during the procedure to the lead placement site. In some examples, the planned path of travel may extend from outside of patient 12, through access site 46, through layers of diaphragmatic attachments 44, through the substernal space of patient 12, and toward the lead placement site (e.g., lead placement site 144 of FIG. 6) within anterior mediastinum 34, such as along line 48. As the clinician advances elongate body 92 toward the lead placement site, progress bar 232 populates with fill 234, which may represent the position of elongate body 92 within patient 12.

In some examples, fill 234 may have a color or pattern having visible contrast with an unfilled portion of progress bar 232, which may aid the clinician in observing the progress of elongate body 92. In some examples, fill 234 may change color or pattern when fill 234 reaches certain points along progress bar 232. For example, a color of fill 234 may change when fill 234 reaches a first layer of diaphragmatic attachments 44, when fill 234 crosses one or more additional layers of diaphragmatic attachments 44, when fill 234 reaches the substernal space of patient 12, and/or when fill 234 reaches the lead implantation site. In some examples, fill 234 may include a marker 236, such as a line or other visible marker, that represents the position of distal end 96 of elongate body 92. In any such examples, processing circuitry 135 of monitoring system 134 may determine the position of distal end 96 of elongate body 92 as elongate body 92 is advanced based on one or more signals corresponding to a pressure of a fluid within fluid lumen 134 sensed by pressure sensor 106 and cause user interface 137 to populate progress bar 232 with fill 234 and/or marker 236 accordingly.

In some examples, GUI 230 may include information box 238, which may contain a text-based indication of a number of layers of diaphragmatic attachments 44 that distal end 96 of elongate body 92 has crossed, a number of layers of diaphragmatic attachments 44 that remain uncrossed by distal end 96 of elongate body 92, an indication that all layers of diaphragmatic attachments 44 have been crossed, and/or other information pertaining to the position of elongate body 92. GUI 230 may include instruction box 240, in addition to or instead of information box 238, which may contain a text-based instruction to the clinician. Such an instruction may be an instruction to continue advancing elongate body 92, an instruction to withdraw elongate body 92 (e.g., if distal end 96 of elongate body 92 is less than a threshold distance from heart 26), an instruction to change the direction of advancement of elongate body 92, or an instruction to stop advancing elongate body 92. In any such examples, GUI 230 may help the clinician to efficiently and safely carry out a procedure to implant a medical lead by providing a real-time visible indication of the position of elongate body 92 during the procedure.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A system for determining a position of a medical device relative to a plurality of diaphragmatic attachment layers of a patient, the system comprising:
   the medical device comprising:
   an elongate body defining a proximal end and a distal end configured to advance through the plurality of diaphragmatic attachment layers; and
   at least one pressure sensor, wherein the at least one pressure sensor is configured to sense a pressure during a medical procedure to advance the elongate body through the plurality of diaphragmatic attachment layers of the patient into an anterior mediastinum, the sensed pressure being at least one of a pressure within the elongate body or at the distal end of the elongate body; and
   processing circuitry configured to:
   receive, from the at least one pressure sensor, a signal corresponding to the pressure at each of a plurality of time points during the medical procedure;
   determine, for each of the plurality of time points, a corresponding amplitude value of the signal;
   determine a difference between two amplitude values of the signal; determine an amplitude oscillation status of the signal, the amplitude oscillation status being associated with respiratory cycles of the patient;
   determine, based on the difference between the two amplitude values and the amplitude oscillation status, a position of the distal end of the elongate body relative to individual attachment layers of the plurality of diaphragmatic attachment layers; and
   provide, via a user interface, an indication of the position of the distal end of the elongate body relative to the individual attachment layers of the plurality of diaphragmatic attachment layers.

2. The system of claim 1, wherein the processing circuitry is further configured to provide, via the user interface, an indication of the pressure at each of the plurality of time points.

3. The system of claim 1, wherein the user interface comprises a display device, and the processing circuitry is configured to cause the display device to display a graphical user interface comprising:
   a pressure waveform depicting the pressure at each of the plurality of time points based on the signal corresponding to the pressure at each of the plurality of time points; and
   a visible indication of the position of the distal end of the elongate body relative to the individual attachment layers of the plurality of diaphragmatic attachment layers.

4. The system of claim 1, wherein the processing circuitry is further configured to control the user interface to generate an audible indication of the position of the distal end of the elongate body relative to the individual attachment layers of the plurality of diaphragmatic attachment layers.

5. The system of claim 1, wherein the amplitude oscillation status comprises an absence of oscillations associated with respiration in the amplitude values of the signal, and wherein the absence of the oscillations is associated with the position of the distal end of the elongate body comprising a position superficial to at least one attachment layer of the plurality of diaphragmatic attachment layers.

6. The system of claim 1, wherein the amplitude oscillation status comprises a presence of at least one oscillation in the amplitude values of the signal, wherein the at least one oscillation is associated with respiration, and wherein the presence of the at least one oscillation is associated with the position of the distal end of the elongate body comprising a position deep to each layer of the plurality of diaphragmatic attachment layers.

7. The system of claim 1, wherein the difference between the two amplitude values of the signal corresponds to a decrease in the pressure that is associated with movement of the distal end of the elongate body from a first position within an individual attachment layer of the plurality of diaphragmatic attachment layers to a second position deep to the individual attachment layer of the plurality of diaphragmatic attachment layers.

8. The system of claim 7, wherein the two of the plurality of amplitude values are a first two of the plurality of amplitude values, the two of the plurality of time points are a first two of the plurality of time points, the decrease in the pressure is a first decrease in the pressure, and the layer of the plurality of diaphragmatic attachment layers is a first layer of the plurality of diaphragmatic attachment layers, and wherein the processing circuitry is further configured to determine a difference between a second two of the plurality of amplitude values of the signal that correspond to a second two of the plurality of time points corresponds to a second decrease in the pressure that is associated with movement of the distal end of the elongate body from a third position within a second layer of the plurality of diaphragmatic attachment layers to a fourth position deep to the second layer of the plurality of diaphragmatic attachment layers, the second layer deep to the first layer.

9. The system of claim 8, wherein the fourth position deep to the second layer of the plurality of diaphragmatic attachment layers comprises a position deep to each layer of the plurality of diaphragmatic attachment layers.

10. The system of claim 1, wherein the elongate body further defines a first lumen extending at least partially through the elongate body to the distal end, the medical device further comprising a fluid line connected to the elongate body and defining a second lumen in fluid communication with the first lumen, wherein the fluid line is configured to supply a fluid to the first lumen, wherein the pressure is a pressure of the fluid, and wherein the signal corresponding to the pressure at each of the plurality of time points comprises a signal corresponding to the pressure of the fluid at each of the plurality of time points.

11. The system of claim 10, wherein the at least one sensor is positioned within at least one of the first lumen or the second lumen.

12. The system of claim 10, wherein the elongate body comprises a hub configured to receive the fluid line, wherein the first lumen extends through the hub, and wherein the second lumen is in fluid communication with the first lumen via the hub.

13. The system of claim 1, wherein the at least one pressure sensor is positioned near the distal end of the elongate body.

14. The system of claim 1, wherein the elongate body comprises a needle, and wherein the distal end comprises a sharp cutting tip.

15. The system of claim 14, wherein the elongate body comprises a tunneling shaft, and wherein the distal end comprises a blunt tip.

16. The system of claim 14, further comprising a handle positioned at the proximal end of the elongate body.

17. The system of claim 14, wherein the elongate body is flexible and further defines a third lumen, the medical device further comprising a shaping member removably insertable within the third lumen and movable to a plurality of locations within the third lumen, the shaping member configured to retain the elongate body and the shaping member in a second, bent shape when the flexible elongate body and the shaping member are bent from a first shape to the second shape.

18. The system of claim 14, wherein the distal end of the elongate body is further configured to advance into the anterior mediastinum of the patient.

19. The system of claim 14, wherein the processing circuitry is configured to:
determine, based on the difference between the two amplitude values and the amplitude oscillation status, the distal end of the elongate body relative is positioned beyond a first layer of the plurality of diaphragmatic attachment layers but not beyond a second layer of the plurality of diaphragmatic attachment layers, and
provide, via the user interface, an indication of the position of the distal end of the elongate body being beyond the first layer of the plurality of diaphragmatic attachment layers but not being beyond a second layer of the plurality of diaphragmatic attachment layers.

20. A method for determining a position of a medical device relative to a plurality of diaphragmatic attachment layers of a patient, the medical device comprising:
an elongate body defining a proximal end and a distal end configured to advance through the plurality of diaphragmatic attachment layers;
at least one pressure sensor, wherein the at least one pressure sensor is configured to sense a pressure while advancing the elongate body through the plurality of diaphragmatic attachment layers of a patient into an anterior mediastinum,
the sensed pressure being at least one of a pressure within the elongate body or at the distal end of the elongate body: and the method comprising, by processing circuitry of a medical device system comprising the medical device;
receiving, from the at least one pressure sensor, a signal corresponding to the pressure at each of a plurality of time points during the medical procedure;
determining, for each of the plurality of time points, a corresponding amplitude value of the signal;
determining a difference between two amplitude values of the signal; determining an amplitude oscillation status of the signal, the amplitude oscillation status being associated with respiratory cycles of the patient;
determining, based on the difference between the two amplitude values and the amplitude oscillation status, a position of the distal end of the elongate body relative to individual attachment layers of the plurality of diaphragmatic attachment layers; and
providing, via a user interface, an indication of the position of the distal end of the elongate body relative to the individual attachment layers of the plurality of diaphragmatic attachment layers.

21. The method of claim 20, further comprising providing, via the user interface, an indication of the pressure at each of the plurality of time points.

22. The method of claim 20, wherein the user interface comprises a display device, the method further comprising:
causing, by the processing circuitry of the medical device system, the display device to display a graphical user interface comprising: a pressure waveform depicting the pressure at each of the plurality of time points based on the signal corresponding to the pressure at each of the plurality of time points; and
a visible indication of the position of the distal end of the elongate body relative to the individual attachment layers of the plurality of diaphragmatic attachment layers.

23. The method of claim 22, further comprising controlling, by the processing circuitry of the medical device system, the user interface to generate an audible indication of the position of the distal end of the elongate body relative to the individual attachment layers of the plurality of diaphragmatic attachment layers.

24. The method of claim 20, wherein determining the amplitude oscillation status comprises determining an absence of oscillations associated with respiration in the amplitude values of the signal, and wherein the absence of the oscillations is associated with the position of the distal end of the elongate body comprising a position superficial to at least one attachment layer of the plurality of diaphragmatic attachment layers.

25. The method of claim 24, wherein the elongate body is configured to be advanced deep to the at least one layer of the plurality of diaphragmatic attachment layers.

26. The method of claim 25, further comprising, by the processing circuitry and subsequent to further advancing the elongate body deep to the at least one attachment layer of the plurality of diaphragmatic attachment layers, determining the amplitude oscillation status comprises determining a presence of at least one oscillation in the amplitude values of the signal, wherein the at least one oscillation is associated with respiration, and wherein the presence of the at least one oscillation is associated with the position of the distal end of the elongate body comprising a position deep to each layer of the plurality of diaphragmatic attachment layers.

27. The method of claim 26, wherein the medical device system further comprises a sheath positioned around the elongate body, the method further comprising:
  advancing the elongate body superiorly through a substernal space of the patient to a lead placement site;
  withdrawing the elongate body from the sheath; and
  advancing a medical lead through the sheath to the lead placement site.

28. The method of claim 20, wherein the difference between the two amplitude values of the signal corresponds to a decrease in the pressure that is associated with movement of the distal end of the elongate body from a first position within an individual attachment layer of the plurality of diaphragmatic attachment layers to a second position deep to the individual attachment layer of the plurality of diaphragmatic attachment layers.

29. The method of claim 28, wherein the two of the plurality of amplitude values are a first two of the plurality of amplitude values, the two of the plurality of time points are a first two of the plurality of time points, the decrease in the pressure is a first decrease in the pressure, and the layer of the plurality of diaphragmatic attachment layers is a first layer of the plurality of diaphragmatic attachment layers, the method further comprising determining a difference between a second two of the plurality of amplitude values of the signal that correspond to a second two of the plurality of time points corresponds to a second decrease in the pressure of the fluid that is associated with movement of the distal end of the elongate body from a third position within a second layer of the plurality of diaphragmatic attachment layers to a fourth position deep to the second layer of the plurality of diaphragmatic attachment layers, the second layer deep to the first layer.

30. The method of claim 29, wherein the fourth position deep to the second layer of the plurality of diaphragmatic attachment layers comprises a position deep to each layer of the plurality of diaphragmatic attachment layers.

31. The method of claim 20, wherein the elongate body further defines a first lumen extending at least partially through the elongate body to the distal end, the medical device further comprising a fluid line connected to the elongate body and defining a second lumen in fluid communication with the first lumen, wherein the fluid line is configured to supply a fluid to the first lumen, wherein the pressure is a pressure of the fluid, and wherein the signal corresponding to the pressure at each of the plurality of time points comprises a signal corresponding to the pressure of the fluid at each of the plurality of time points.

32. The method of claim 31, wherein the at least one sensor is positioned within at least one of the first lumen or the second lumen.

33. The method of claim 31, wherein the elongate body comprises a hub configured to receive the fluid line, wherein the first lumen extends through the hub, and wherein the second lumen is in fluid communication with the first lumen via the hub.

34. The method of claim 20, wherein the at least one pressure sensor is positioned near the distal end of the elongate body.

35. The method of claim 20, wherein the elongate body comprises a needle, and wherein the distal end comprises a sharp cutting tip.

36. The method of claim 20, wherein the elongate body comprises a tunneling shaft, and wherein the distal end comprises a blunt tip.

37. The method of claim 20, further comprising a handle positioned at the proximal end of the elongate body.

38. The method of claim 20, wherein the elongate body is flexible and further defines a third lumen, the medical device further comprising a shaping member removably insertable within the third lumen and movable to a plurality of locations within the third lumen, the shaping member configured to retain the elongate body and the shaping member in a second, bent shape when the flexible elongate body and the shaping member are bent from a first shape to the second shape.

39. The method of claim 20, wherein the distal end of the elongate body is further configured to advance into the anterior mediastinum of the patient.

40. The method of claim 20, wherein determining the position of the distal end of the elongate body comprises determining, based on the difference between the two amplitude values and the amplitude oscillation status, the distal end of the elongate body relative is positioned beyond a first layer of the plurality of diaphragmatic attachment layers but not beyond a second layer of the plurality of diaphragmatic attachment layers, and wherein providing the indication of the position of the distal end of the elongate body comprises providing, via the user interface, an indication of the position of the distal end of the elongate body being beyond the first layer of the plurality of diaphragmatic attachment layers but not being beyond a second layer of the plurality of diaphragmatic attachment layers.

41. A medical device comprising:
  an elongate body defining a proximal end and a distal end configured to advance through a plurality of diaphragmatic attachment layers, and a first lumen extending at least partially through the elongate body to the distal end; and
  at least one pressure sensor, wherein the at least one pressure sensor is configured to sense a pressure during a medical procedure to advance the elongate body through a plurality of diaphragmatic attachment layers of a patient and transmit to processing circuitry, at each of a plurality of time points during the medical procedure, a signal corresponding to the pressure, wherein a difference between two values of the signal and an amplitude oscillation status of the signal is associated with a position of the distal end of the elongate body relative to individual attachment layers of the plurality of diaphragmatic attachment layers.

* * * * *